US008734808B2

(12) United States Patent
Kapil

(10) Patent No.: US 8,734,808 B2
(45) Date of Patent: May 27, 2014

(54) ISOLATION OF A VIRUS RELATED TO CANINE PARVOVIRUS-2 FROM A RACCOON

(75) Inventor: Sanjay Kapil, Stillwater, OK (US)

(73) Assignee: The Board of Regents for Oklahoma State University, Stillwater, OK (US)

(*) Notice: Subject to any disclaimer, the term of this patent is extended or adjusted under 35 U.S.C. 154(b) by 0 days.

(21) Appl. No.: 13/501,895

(22) PCT Filed: Oct. 14, 2010

(86) PCT No.: PCT/US2010/052677
§ 371 (c)(1), (2), (4) Date: Apr. 13, 2012

(87) PCT Pub. No.: WO2011/047158
PCT Pub. Date: Apr. 21, 2011

(65) Prior Publication Data

US 2012/0201848 A1 Aug. 9, 2012

Related U.S. Application Data

(60) Provisional application No. 61/251,432, filed on Oct. 14, 2009.

(51) Int. Cl.
*A61K 39/12* (2006.01)
*A61K 39/23* (2006.01)
*C07K 14/015* (2006.01)

(52) U.S. Cl.
USPC .................. 424/202.1; 424/233.1; 435/235.1; 435/320.1; 530/350; 536/23.72

(58) Field of Classification Search
CPC ....... A61K 39/12; A61K 39/23; C07K 14/015
See application file for complete search history.

(56) References Cited

U.S. PATENT DOCUMENTS

| | | | | |
|---|---|---|---|---|
| 4,904,468 | A * | 2/1990 | Gill et al. | 424/202.1 |
| 5,756,103 | A | 5/1998 | Paoletti et al. | |
| 5,885,585 | A | 3/1999 | Parrish et al. | |
| 7,736,658 | B2 * | 6/2010 | Dominowski et al. | 424/201.1 |
| 2008/0014260 | A1 * | 1/2008 | Seager | 424/458 |
| 2012/0201848 | A1 * | 8/2012 | Kapil | 424/202.1 |

FOREIGN PATENT DOCUMENTS

| | | | |
|---|---|---|---|
| CN | 101035558 | A1 | 9/2007 |
| EP | 0 863151 | A1 | 9/1998 |
| WO | WO 2008/157236 | A1 | 12/2008 |

OTHER PUBLICATIONS

Nakamura et al. (Archives of Virology. 2004; 149: 2261-2269).*

EF599098.2. NCBI-GenBank (online) Feb. 2008 [retrieved on Dec. 29, 2010] Retrieved from the Internet URL:<http://www.ncbi.nim.nih.gov/nucleotide/160250242?report=genbank&log$=nuclalign&blast_rank=86&RID=H1ZCHUHG01P. See nucleotide sequence and amino acid sequence.

Q98VH1. VP2. NCBI-GenBank (online) Nov. 28, 2006 [retrieved on Dec. 20, 2010] Retrieved from the Internet URL: <http://www.ncbi.nim.nih.gov/protein/81965481>. See amino acid sequence.

Ikeda et al., "Predominance of Canine Parvovirus (CPV) in Unvaccinated Cat Populations and Emergence of New Antigenic Types of CPVs in Cats", "Virology", 2000, pp. 13-19, vol. 278, Publisher: Academic Press, Published in: US.

"PCT International Search Report, Application No. PCT/US2010/52677, mailed Jan. 13, 2011".

"PCT Written Opinion, Application No. PCT/US2010/52677, mailed Jan. 13, 2011".

Allison, et al., "Role of Multiple Hosts in the Cross-Species Transmission and Emergence of a Pandemic Parvovirus", Nov. 9, 2011, pp. 865-872, vol. 86, No. 2, Publisher: Journal of Virology, Published in: US.

Allison, Andrew et al., "Frequent Cross-Species Transmission of Parvoviruses Among Diverse Carnivore Hosts", Feb. 2013, pp. 2342-2347, vol. 87, No. 4, Publisher: Journal of Virology, Published in: US.

Kang, et al., "Prevalance and Genetic Characterization of Canine Parvoviruses in Korea", Jan. 3, 2008, vol. 36, No. 1, Publisher: Virus Genes, Kluwer Academic Publishers, Published in: US.

Harbison, et al., "The Parvovirus Capsid Odyssey: From the Cell Surface to the Nucleus", May 1, 2008, vol. 16, No. 5, Publisher: Trends in Microbiology, Elsevier Science Ltd., Published in: GB.

Parrish et al., "Canine Host Range and a Specific Epitope Map Along With Variant Sequences in the Capsid Protein Gene of Canine Parvoviru", Oct. 1, 1998, pp. 293-307, vol. 166, No. 2, Publisher: Virology, Elsevier, Amsterdam, NL, Published in: NL.

EP10824094, Supplementary European Search Report, Feb. 12, 2013.

Mochizuki, et al., "Isolation of a Canine Parvovirus From a Cat Manifesting Clinical Signs of Feline Panleukopenia", Sep. 1996, pp. 2101-2105, vol. 34, No. 9, Publisher: Journal of Clinical Microbiology, Published in: US.

Tsai, Chich H., et al., "Localization of the VP2 Protein of Canine Parvovirus Type 2 on the Baculovirus Envelop and Its Immunogenicity in a Mouse Model", Dec. 2012, pp. 178-185, No. 2, Published in: US.

* cited by examiner

*Primary Examiner* — Shannon A Foley
(74) *Attorney, Agent, or Firm* — Fellers, Snider, Blankenship, Bailey & Tippens, P.C.; Terry L. Watt

(57) ABSTRACT

Vaccines preparations against canine parvovirus are provided. The vaccines include a novel canine parvovirus-2 isolated from a raccoon, and related nucleic acids and proteins.

13 Claims, 12 Drawing Sheets

```
ATGAGTGATGGAGCAGTTCAACCAGACGGTGGTCAACCTGCTGTCAGAAATGAAA
GAGCTACAGGATCTGGGAACGGGTCTGGAGGCGGGGGTGGTGGTGGTTCTGGGGG
TGTGGGGATTTCTACGGGTACTTTCAATAATCAGACGGAATTTAAATTTTTGGAA
AACGGATGGGTGGAAATCACAGCAAACTCAAGCAGACTTGTACATTTAAATATGC
CAGAAAGTGAAAATTATAGAAGAGTGGTTGTAAATAATTTAGATAAAACTGCAGT
TAACGGAAACATGGCTTTAGATGATACTCATGCACAAATTGTAACACCTTGGTCA
TTGGTTGATGCAAATGCTTGGGGAGTTTGGTTTAATCCAGGAGATTGGCAACTAA
TTGTTAATACTATGAGTGAGTTGCATTTAGTTAGTTTTGAACAAGAAATTTTTAA
TGTTGTTTTAAAGACTGTTTCAGAATCTGCTACTCAGCCACCAACTAAAGTTTAT
AATAATGATTTAACTGCATCATTGATGGTTGCATTAGATAGTAATAATACTATGC
CATTTACTCCAGCAGCTATGAGATCTGAGACATTGGGTTTTTATCCATGGAAACC
AACCATACCAACTCCATGGAGATATTATTTTCAATGGGATAGAACATTAATACCA
TCTCATACTGGAACTAGTGGCACACCAACAAATACATACCATGGTACAGATCCAG
ATGATGTTCAATTTTATACTATTGAAAATTCTGTGCCAGTACACTTACTAAGAAC
AGGTGATGAATTTGCTACAGGAACATTTTTTTTTGATTGTAAACCATGTAGACTA
ACACATACATGGCAAACAAATAGAGCATTGGGCTTACCACCATTTCTAAATTCTT
TGCCTCAATCTGAAGGAGATACTAACTTTGGTGATATAGGAATTCAACAAGATAA
AAGACGTGGTGTAACTCAAATGGGAAATACAAACTATATTACTGAAGCTACTATT
ATGAGACCAGCTGAGGTTGGTTATAGTGCACCATATTATTCTTTTGAGGCGTCTA
CACAAGGGCCATTTAAAACACCTATTGCAGCAGGACGGGGGGGAGCGCAAACAGA
TGAAAATCAAGCAGCAGATGGTGATCCAAGATATGCATTTGGTAGACAACATGGT
CAAAAAACTACCACAACAGGAGAAACACCTGAGAGATTTACATATATAGCACATC
AAGATACAGGAAGATATCCAGAAGGAGATTGGATTCAAAATATTAACTTTAACCT
TCCTGTAANAAATGATAATGTATTGCTACCAACAGATCCAATTGGAGGTAAAACA
GGAATTAACTATACTAATATATTTAATACTTATGGTCCTTTAACTGCATTAAATA
ATGTACCACCAGTTTATCCAAATGGTCAAATTTGGGATAAAGAATTTGATACTGA
CTTAAAACCAAGACTTCATGTAAATGCACCATTTGTTTGTCAAAATAATTGTCCT
GGTCAATTATTTGTAAAAGTTGCGCCTAATTTAACAAATGAATATGATCCTGATG
CATCTGCTAATATGTCAAGAATTGTAACTTACTCAGATTTTTGGTGGAAAGGTAA
ATTAGTATTTAAAGCTAAACTAAGAGCCTCTCATACTTGGAATCCAATTCAACAA
ATGAGTATTAATGTAGATAACCAATTTAACTATGTACCAAGTAATATTGGAGGTA
TGAAAATTGTATATGAAAATCTCAACTAGCACCTAGAAAATTATATTAACATAC
TTACTATGTTTTTATGTTTATTACATATCAACTAGCACCA
```

(SEQ ID NO: 1)

Figure 2A

ATGAGTGATGGAGCAGTTCAACCAGACGGTGGTCAACCTGCTGTCAGAAATGAAA
GAGCTACAGGATCTGGGAACGGGTCTGGAGGCGGGGGTGGTGGTGGTTCTGGGGG
TGTGGGGATTTCTACGGGTACTTTCAATAATCAGACGGAATTTAAATTTTTGGAA
AACGGATGGGTGGAAATCACAGCAAACTCAAGCAGACTTGTACATTTAAATATGC
CAGAAAGTGAAAATTATAGAAGAGTGGTTGTAAATAATTTAGATAAAACTGCAGT
TAACGGAAACATGGCTTTAGATGATACTCATGCACAAATTGTAACACCTTGGTCA
TTGGTTGATGCAAATGCTTGGGGAGTTTGGTTTAATCCAGGAGATTGGCAACTAA
TTGTTAATACTATGAGTGAGTTGCATTTAGTTAGTTTTGAACAAGAAATTTTTAA
TGTTGTTTTAAAGACTGTTTCAGAATCTGCTACTCAGCCACCAACTAAAGTTTAT
AATAATGATTTAACTGCATCATTGATGGTTGCATTAGATAGTAATAATACTATGC
CATTTACTCCAGCAGCTATGAGATCTGAGACATTGGGTTTTTATCCATGGAAACC
AACCATACCAACTCCATGGAGATATTATTTTCAATGGGATAGAACATTAATACCA
TCTCATACTGGAACTAGTGGCACACCAACAAATACATACCATGGTACAGATCCAG
ATGATGTTCAATTTTATACTATTGAAAATTCTGTGCCAGTACACTTACTAAGAAC
AGGTGATGAATTTGCTACAGGAACATTTTTTTTGATTGTAAACCATGTAGACTA
ACACATACATGGCAAACAAATAGAGCATTGGGCTTACCACCATTTCTAAATTCTT
TGCCTCAATCTGAAGGAGATACTAACTTTGGTGATATAGGAATTCAACAAGATAA
AAGACGTGGTGTAACTCAAATGGGAAATACAAACTATATTACTGAAGCTACTATT
ATGAGACCAGCTGAGGTTGGTTATAGTGCACCATATTATTCTTTTGAGGCGTCTA
CACAAGGGCCATTTAAAACACCTATTGCAGCAGGACGGGGGGGAGCGCAAACAGA
TGAAAATCAAGCAGCAGATGGTGATCCAAGATATGCATTTGGTAGACAACATGGT
CAAAAAACTACCACAACAGGAGAAACACCTGAGAGATTTACATATATAGCACATC
AAGATACAGGAAGATATCCAGAAGGAGATTGGATTCAAAATATTAACTTTAACCT
TCCTGTAANAAATGATAATGTATTGCTACCAACAGATCCAATTGGAGGTAAAACA
GGAATTAACTATACTAATATATTTAATACTTATGGTCCTTTAACTGCATTAAATA
ATGTACCACCAGTTTATCCAAATGGTCAAATTTGGGATAAAGAATTTGATACTGA
CTTAAAACCAAGACTTCATGTAAATGCACCATTTGTTTGTCAAAATAATTGTCCT
GGTCAATTATTTGTAAAAGTTGCGCCTAATTTAACAAATGAATATGATCCTGATG
CATCTGCTAATATGTCAAGAATTGTAACTTACTCAGATTTTTGGTGGAAAGGTAA
ATTAGTATTTAAAGCTAAACTAAGAGCCTCTCATACTTGGAATCCAATTCAACAA
ATGAGTATTAATGTAGATAACCAATTTAACTATGTACCAAGTAATATTGGAGGTA
TGAAAATTGTATATGAAAAATCTCAACTAGCACCTAGAAAATTATAT (SEQ ID NO: 2)

Figure 2B

| | | | | | | | | | | | | | | | |
|---|---|---|---|---|---|---|---|---|---|---|---|---|---|---|---|
| Met | Ser | Asp | Gly | Ala | Val | Gln | Pro | Asp | Gly | Gly | Gln | Pro | Ala | Val | Arg |
| 1 | | | | 5 | | | | | 10 | | | | | 15 | |
| Asn | Glu | Arg | Ala | Thr | Gly | Ser | Gly | Asn | Gly | Ser | Gly | Gly | Gly | Gly | Gly |
| | | | 20 | | | | | 25 | | | | | 30 | | |
| Gly | Gly | Ser | Gly | Gly | Val | Gly | Ile | Ser | Thr | Gly | Thr | Phe | Asn | Asn | Gln |
| | | 35 | | | | | 40 | | | | | 45 | | | |
| Thr | Glu | Phe | Lys | Phe | Leu | Glu | Asn | Gly | Trp | Val | Glu | Ile | Thr | Ala | Asn |
| | 50 | | | | | 55 | | | | | 60 | | | | |
| Ser | Ser | Arg | Leu | Val | His | Leu | Asn | Met | Pro | Glu | Ser | Glu | Asn | Tyr | Arg |
| 65 | | | | | 70 | | | | | 75 | | | | | 80 |
| Arg | Val | Val | Val | Asn | Asn | Leu | Asp | Lys | Thr | Ala | Val | Asn | Gly | Asn | Met |
| | | | | 85 | | | | | 90 | | | | | 95 | |
| Ala | Leu | Asp | Asp | Thr | His | Ala | Gln | Ile | Val | Thr | Pro | Trp | Ser | Leu | Val |
| | | | 100 | | | | | 105 | | | | | 110 | | |
| Asp | Ala | Asn | Ala | Trp | Gly | Val | Trp | Phe | Asn | Pro | Gly | Asp | Trp | Gln | Leu |
| | | 115 | | | | | 120 | | | | | 125 | | | |
| Ile | Val | Asn | Thr | Met | Ser | Glu | Leu | His | Leu | Val | Ser | Phe | Glu | Gln | Glu |
| | 130 | | | | | 135 | | | | | 140 | | | | |
| Ile | Phe | Asn | Val | Val | Leu | Lys | Thr | Val | Ser | Glu | Ser | Ala | Thr | Gln | Pro |
| 145 | | | | | 150 | | | | | 155 | | | | | 160 |
| Pro | Thr | Lys | Val | Tyr | Asn | Asn | Asp | Leu | Thr | Ala | Ser | Leu | Met | Val | Ala |
| | | | | 165 | | | | | 170 | | | | | 175 | |
| Leu | Asp | Ser | Asn | Asn | Thr | Met | Pro | Phe | Thr | Pro | Ala | Ala | Met | Arg | Ser |
| | | | 180 | | | | | 185 | | | | | 190 | | |
| Glu | Thr | Leu | Gly | Phe | Tyr | Pro | Trp | Lys | Pro | Thr | Ile | Pro | Thr | Pro | Trp |
| | | 195 | | | | | 200 | | | | | 205 | | | |
| Arg | Tyr | Tyr | Phe | Gln | Trp | Asp | Arg | Thr | Leu | Ile | Pro | Ser | His | Thr | Gly |
| | 210 | | | | | 215 | | | | | 220 | | | | |
| Thr | Ser | Gly | Thr | Pro | Thr | Asn | Thr | Tyr | His | Gly | Thr | Asp | Pro | Asp | Asp |
| 225 | | | | | 230 | | | | | 235 | | | | | 240 |
| Val | Gln | Phe | Tyr | Thr | Ile | Glu | Asn | Ser | Val | Pro | Val | His | Leu | Leu | Arg |
| | | | | 245 | | | | | 250 | | | | | 255 | |
| Thr | Gly | Asp | Glu | Phe | Ala | Thr | Gly | Thr | Phe | Phe | Phe | Asp | Cys | Lys | Pro |
| | | | 260 | | | | | 265 | | | | | 270 | | |
| Cys | Arg | Leu | Thr | His | Thr | Trp | Gln | Thr | Asn | Arg | Ala | Leu | Gly | Leu | Pro |
| | | 275 | | | | | 280 | | | | | 285 | | | |
| Pro | Phe | Leu | Asn | Ser | Leu | Pro | Gln | Ser | Glu | Gly | Asp | Thr | Asn | Phe | Gly |
| | 290 | | | | | 295 | | | | | 300 | | | | |
| Asp | Ile | Gly | Ile | Gln | Gln | Asp | Lys | Arg | Arg | Gly | Val | Thr | Gln | Met | Gly |
| 305 | | | | | 310 | | | | | 315 | | | | | 320 |
| Asn | Thr | Asn | Tyr | Ile | Thr | Glu | Ala | Thr | Ile | Met | Arg | Pro | Ala | Glu | Val |
| | | | | 325 | | | | | 330 | | | | | 335 | |

FIGURE 3A

```
Gly Tyr Ser Ala Pro Tyr Tyr Ser Phe Glu Ala Ser Thr Gln Gly Pro
            340                 345                 350

Phe Lys Thr Pro Ile Ala Ala Gly Arg Gly Gly Ala Gln Thr Asp Glu
        355                 360                 365

Asn Gln Ala Ala Asp Gly Asp Pro Arg Tyr Ala Phe Gly Arg Gln His
    370                 375                 380

Gly Gln Lys Thr Thr Thr Thr Gly Glu Thr Pro Glu Arg Phe Thr Tyr
385                 390                 395                 400

Ile Ala His Gln Asp Thr Gly Arg Tyr Pro Glu Gly Asp Trp Ile Gln
                405                 410                 415

Asn Ile Asn Phe Asn Leu Pro Val Xaa Asn Asp Asn Val Leu Leu Pro
            420                 425                 430

Thr Asp Pro Ile Gly Gly Lys Thr Gly Ile Asn Tyr Thr Asn Ile Phe
        435                 440                 445

Asn Thr Tyr Gly Pro Leu Thr Ala Leu Asn Asn Val Pro Pro Val Tyr
    450                 455                 460

Pro Asn Gly Gln Ile Trp Asp Lys Glu Phe Asp Thr Asp Leu Lys Pro
465                 470                 475                 480

Arg Leu His Val Asn Ala Pro Phe Val Cys Gln Asn Asn Cys Pro Gly
                485                 490                 495

Gln Leu Phe Val Lys Val Ala Pro Asn Leu Thr Asn Glu Tyr Asp Pro
            500                 505                 510

Asp Ala Ser Ala Asn Met Ser Arg Ile Val Thr Tyr Ser Asp Phe Trp
        515                 520                 525

Trp Lys Gly Lys Leu Val Phe Lys Ala Lys Leu Arg Ala Ser His Thr
    530                 535                 540

Trp Asn Pro Ile Gln Gln Met Ser Ile Asn Val Asp Asn Gln Phe Asn
545                 550                 555                 560

Tyr Val Pro Ser Asn Ile Gly Gly Met Lys Ile Val Tyr Glu Lys Ser
                565                 570                 575

Gln Leu Ala Pro Arg Lys Leu Tyr His Thr Tyr Tyr Val Phe Met Phe
            580                 585                 590

Ile Thr Tyr Gln Pro Ser Thr
        595
```

FIGURE 3A (con't)

```
Met Ser Asp Gly Ala Val Gln Pro Asp Gly Gly Gln Pro Ala Val Arg
1               5                   10                  15

Asn Glu Arg Ala Thr Gly Ser Gly Asn Gly Ser Gly Gly Gly Gly Gly
            20                  25                  30

Gly Gly Ser Gly Gly Val Gly Ile Ser Thr Gly Thr Phe Asn Asn Gln
        35                  40                  45

Thr Glu Phe Lys Phe Leu Glu Asn Gly Trp Val Glu Ile Thr Ala Asn
    50                  55                  60

Ser Ser Arg Leu Val His Leu Asn Met Pro Glu Ser Glu Asn Tyr Arg
65                  70                  75                  80

Arg Val Val Val Asn Asn Leu Asp Lys Thr Ala Val Asn Gly Asn Met
                85                  90                  95

Ala Leu Asp Asp Thr His Ala Gln Ile Val Thr Pro Trp Ser Leu Val
            100                 105                 110

Asp Ala Asn Ala Trp Gly Val Trp Phe Asn Pro Gly Asp Trp Gln Leu
        115                 120                 125

Ile Val Asn Thr Met Ser Glu Leu His Leu Val Ser Phe Glu Gln Glu
    130                 135                 140

Ile Phe Asn Val Val Leu Lys Thr Val Ser Glu Ser Ala Thr Gln Pro
145                 150                 155                 160

Pro Thr Lys Val Tyr Asn Asn Asp Leu Thr Ala Ser Leu Met Val Ala
                165                 170                 175

Leu Asp Ser Asn Asn Thr Met Pro Phe Thr Pro Ala Ala Met Arg Ser
            180                 185                 190

Glu Thr Leu Gly Phe Tyr Pro Trp Lys Pro Thr Ile Pro Thr Pro Trp
        195                 200                 205

Arg Tyr Tyr Phe Gln Trp Asp Arg Thr Leu Ile Pro Ser His Thr Gly
    210                 215                 220

Thr Ser Gly Thr Pro Thr Asn Thr Tyr His Gly Thr Asp Pro Asp Asp
225                 230                 235                 240

Val Gln Phe Tyr Thr Ile Glu Asn Ser Val Pro Val His Leu Leu Arg
                245                 250                 255

Thr Gly Asp Glu Phe Ala Thr Gly Thr Phe Phe Phe Asp Cys Lys Pro
            260                 265                 270

Cys Arg Leu Thr His Thr Trp Gln Thr Asn Arg Ala Leu Gly Leu Pro
        275                 280                 285

Pro Phe Leu Asn Ser Leu Pro Gln Ser Glu Gly Asp Thr Asn Phe Gly
    290                 295                 300

Asp Ile Gly Ile Gln Gln Asp Lys Arg Arg Gly Val Thr Gln Met Gly
305                 310                 315                 320

Asn Thr Asn Tyr Ile Thr Glu Ala Thr Ile Met Arg Pro Ala Glu Val
                325                 330                 335
```

FIGURE 3B

```
Gly Tyr Ser Ala Pro Tyr Tyr Ser Phe Glu Ala Ser Thr Gln Gly Pro
            340                 345                 350

Phe Lys Thr Pro Ile Ala Ala Gly Arg Gly Gly Ala Gln Thr Asp Glu
        355                 360                 365

Asn Gln Ala Ala Asp Gly Asp Pro Arg Tyr Ala Phe Gly Arg Gln His
    370                 375                 380

Gly Gln Lys Thr Thr Thr Thr Gly Glu Thr Pro Glu Arg Phe Thr Tyr
385                 390                 395                     400

Ile Ala His Gln Asp Thr Gly Arg Tyr Pro Glu Gly Asp Trp Ile Gln
                405                 410                 415

Asn Ile Asn Phe Asn Leu Pro Val Xaa Asn Asp Asn Val Leu Leu Pro
            420                 425                 430

Thr Asp Pro Ile Gly Gly Lys Thr Gly Ile Asn Tyr Thr Asn Ile Phe
        435                 440                 445

Asn Thr Tyr Gly Pro Leu Thr Ala Leu Asn Asn Val Pro Pro Val Tyr
    450                 455                 460

Pro Asn Gly Gln Ile Trp Asp Lys Glu Phe Asp Thr Asp Leu Lys Pro
465                 470                 475                     480

Arg Leu His Val Asn Ala Pro Phe Val Cys Gln Asn Asn Cys Pro Gly
                485                 490                 495

Gln Leu Phe Val Lys Val Ala Pro Asn Leu Thr Asn Glu Tyr Asp Pro
            500                 505                 510

Asp Ala Ser Ala Asn Met Ser Arg Ile Val Thr Tyr Ser Asp Phe Trp
        515                 520                 525

Trp Lys Gly Lys Leu Val Phe Lys Ala Lys Leu Arg Ala Ser His Thr
    530                 535                 540

Trp Asn Pro Ile Gln Gln Met Ser Ile Asn Val Asp Asn Gln Phe Asn
545                 550                 555                     560

Tyr Val Pro Ser Asn Ile Gly Gly Met Lys Ile Val Tyr Glu Lys Ser
                565                 570                 575

Gln Leu Ala Pro Arg Lys Leu Tyr
            580
```

FIGURE 3B (con't)

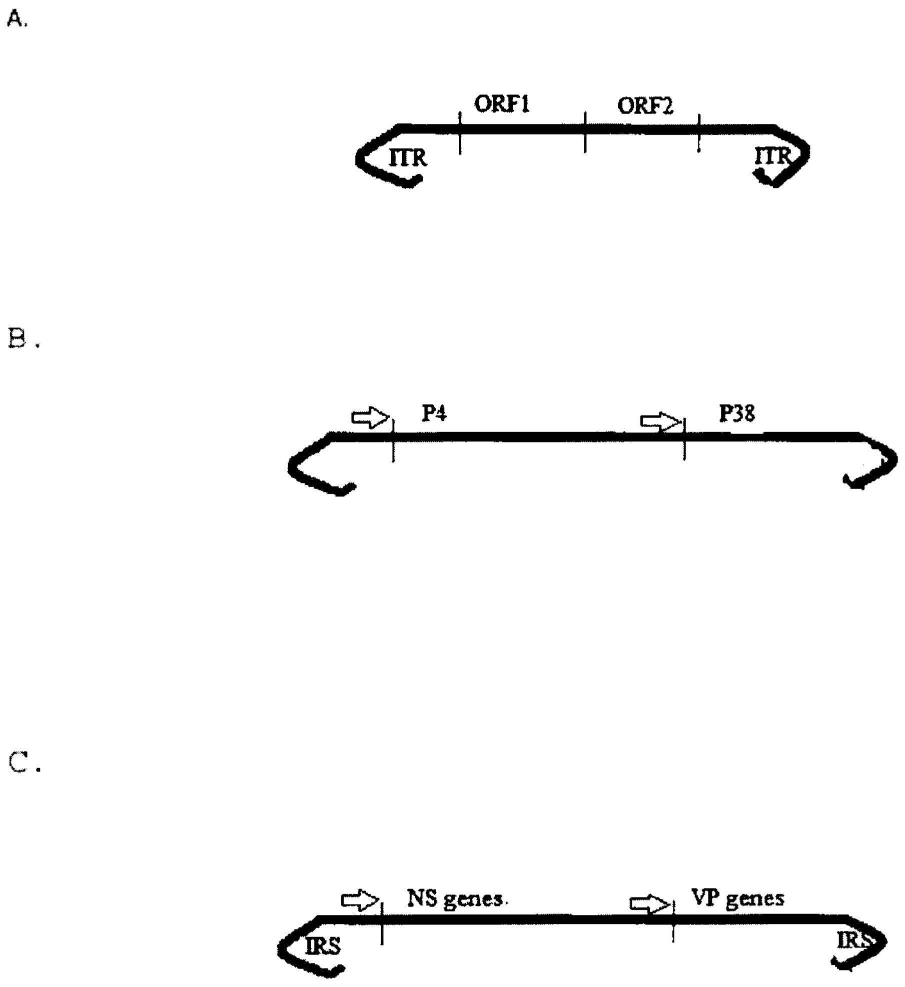
Figure 4A-C

FJ222821:Canine parvovirus 2c strain 56/
FJ222822:Canine parvovirus 2b strain SAH
FJ005259:Canine parvovirus 2a strain 100
FJ005251:Canine parvovirus 2c strain 239
FJ222823:Canine parvovirus 2b strain 29/
08080294RaccoonParvovirus VP-2
FJ222824:Canine parvovirus 2 strain 388/
U39014:ALeutian mink disease parvovirus
FJ440714:Feline panleukopenia virus isol

| Virus | 80 | 87 | 93 | 101 | 103 | 232 | 297 | 300 | 305 | 426 | 555 | 564 | 568 |
|---|---|---|---|---|---|---|---|---|---|---|---|---|---|
| FPV | Lys | Met | Lys | Ile | Val | Val | Ser | Ala | Asp | Asn | Val | Asn | Ala |
| CPV-2 | Arg | Met | Asn | Ile | Val | Ile | Ser | Ala | Asp | Asn | Ile | Ser | Gly |
| CPV-2a | Arg | Leu | Asn | Thr | Ala | Ile | Ser | Gly | Tyr | Asn | Val | Ser | Gly |
| CPV-2b | Arg | Leu | Asn | Thr | Ala | Ile | Ser | Gly | Tyr | Asp | Val | Ser | Gly |
| CPV-2c | Arg | Leu | Asn | Thr | | Ile | Ala | Gly | Tyr | Glu | Val | Ser | Gly |
| MEV | Lys | Leu | Lys | Ile | | Val | Ser | Ala | Asp | Asn | Val | Asn | Ala |
| RPV | Arg | Leu | Asn | Thr | Ala | Thr | Ser | Asp | Asp | Asn | Val | Ser | Gly |

*Fig. 7*

SEQUENCE LISTING

<160> NUMBER OF SEQ ID NOS: 7

<210> SEQ ID NO 1
<211> LENGTH: 1800
<212> TYPE: DNA
<213> ORGANISM: Raccoon parvovirus
<220> FEATURE:
<221> NAME/KEY: misc_feature
<222> LOCATION: (1274)..(1274)
<223> OTHER INFORMATION: n is a, c, g, or t

<400> SEQUENCE: 1

```
atgagtgatg gagcagttca accagacggt ggtcaacctg ctgtcagaaa tgaaagagct      60

acaggatctg ggaacgggtc tggaggcggg ggtggtggtg gttctggggg tgtggggatt     120

tctacgggta ctttcaataa tcagacggaa tttaaatttt tggaaaacgg atgggtggaa     180

atcacagcaa actcaagcag acttgtacat ttaaatatgc cagaaagtga aaattataga     240

agagtggttg taaataattt agataaaact gcagttaacg gaaacatggc tttagatgat     300

actcatgcac aaattgtaac accttggtca ttggttgatg caaatgcttg gggagtttgg     360

tttaatccag gagattggca actaattgtt aatactatga gtgagttgca tttagttagt     420

tttgaacaag aaatttttaa tgttgtttta aagactgttt cagaatctgc tactcagcca     480

ccaactaaag tttataataa tgatttaact gcatcattga tggttgcatt agatagtaat     540

aatactatgc catttactcc agcagctatg agatctgaga cattgggttt ttatccatgg     600

aaaccaacca taccaactcc atggagatat tattttcaat gggatagaac attaatacca     660

tctcatactg gaactagtgg cacaccaaca aatacatacc atggtacaga tccagatgat     720

gttcaatttt atactattga aaattctgtg ccagtacact tactaagaac aggtgatgaa     780

tttgctacag gaacattttt ttttgattgt aaaccatgta gactaacaca tacatggcaa     840

acaaatagag cattgggctt accaccattt ctaaattctt tgcctcaatc tgaaggagat     900

actaactttg gtgatatagg aattcaacaa gataaaagac gtggtgtaac tcaaatggga     960

aatacaaact atattactga agctactatt atgagaccag ctgaggttgg ttatagtgca    1020

ccatattatt cttttgaggc gtctacacaa gggccattta aaacacctat tgcagcagga    1080

cggggggggag cgcaaacaga tgaaaatcaa gcagcagatg gtgatccaag atatgcattt    1140

ggtagacaac atggtcaaaa aactaccaca acaggagaaa cacctgagag atttacatat    1200

atagcacatc aagatacagg aagatatcca gaaggagatt ggattcaaaa tattaacttt    1260

aaccttcctg taanaaatga taatgtattg ctaccaacag atccaattgg aggtaaaaca    1320

ggaattaact atactaatat atttaatact tatggtcctt taactgcatt aaataatgta    1380

ccaccagttt atccaaatgg tcaaatttgg gataaagaat ttgatactga cttaaaacca    1440

agacttcatg taaatgcacc atttgtttgt caaaataatt gtcctggtca attatttgta    1500

aaagttgcgc ctaatttaac aaatgaatat gatcctgatg catctgctaa tatgtcaaga    1560

attgtaactt actcagattt ttggtggaaa ggtaaattag tatttaaagc taaactaaga    1620

gcctctcata cttggaatcc aattcaacaa atgagtatta atgtagataa ccaatttaac    1680

tatgtaccaa gtaatattgg aggtatgaaa attgtatatg aaaaatctca actagcacct    1740

agaaaattat attaacatac ttactatgtt tttatgttta ttacatatca actagcacca    1800
```

<210> SEQ ID NO 2
<211> LENGTH: 1752
<212> TYPE: DNA

<213> ORGANISM: Raccoon parvovirus
<220> FEATURE:
<221> NAME/KEY: misc_feature
<222> LOCATION: (1274)..(1274)
<223> OTHER INFORMATION: n is a, c, g, or t

<400> SEQUENCE: 2

```
atgagtgatg gagcagttca accagacggt ggtcaacctg ctgtcagaaa tgaaagagct     60

acaggatctg ggaacgggtc tggaggcggg ggtggtggtg gttctggggg tgtggggatt    120

tctacgggta ctttcaataa tcagacggaa tttaaatttt tggaaaacgg atgggtggaa    180

atcacagcaa actcaagcag acttgtacat ttaaatatgc cagaaagtga aaattataga    240

agagtggttg taaataattt agataaaact gcagttaacg gaaacatggc tttagatgat    300

actcatgcac aaattgtaac accttggtca ttggttgatg caaatgcttg ggagtttggg    360

tttaatccag gagattggca actaattgtt aatactatga gtgagttgca tttagttagt    420

tttgaacaag aaatttttaa tgttgtttta aagactgttt cagaatctgc tactcagcca    480

ccaactaaag tttataataa tgatttaact gcatcattga tggttgcatt agatagtaat    540

aatactatgc catttactcc agcagctatg agatctgaga cattgggttt ttatccatgg    600

aaaccaacca taccaactcc atggagatat tattttcaat gggatagaac attaatacca    660

tctcatactg gaactagtgg cacaccaaca aatacatacc atggtacaga tccagatgat    720

gttcaatttt atactattga aaattctgtg ccagtacact tactaagaac aggtgatgaa    780

tttgctacag gaacattttt ttttgattgt aaaccatgta gactaacaca tacatggcaa    840

acaaatagag cattgggctt accaccattt ctaaattctt tgcctcaatc tgaaggagat    900

actaactttg gtgatatagg aattcaacaa gataaaagac gtggtgtaac tcaaatggga    960

aatacaaact atattactga agctactatt atgagaccag ctgaggttgg ttatagtgca   1020

ccatattatt cttttgaggc gtctacacaa gggccattta aaacacctat tgcagcagga   1080

cggggggggag cgcaaacaga tgaaaatcaa gcagcagatg gtgatccaag atatgcattt  1140

ggtagacaac atggtcaaaa aactaccaca acaggagaaa cacctgagag atttacatat   1200

atagcacatc aagatacagg aagatatcca gaaggagatt ggattcaaaa tattaacttt   1260

aaccttcctg taanaaatga taatgtattg ctaccaacag atccaattgg aggtaaaaca   1320

ggaattaact atactaatat atttaatact tatggtcctt taactgcatt aaataatgta   1380

ccaccagttt atccaaatgg tcaaatttgg gataaagaat ttgatactga cttaaaacca   1440

agacttcatg taaatgcacc atttgtttgt caaaataatt gtcctggtca attatttgta   1500

aaagttgcgc ctaatttaac aaatgaatat gatcctgatg catctgctaa tatgtcaaga   1560

attgtaactt actcagattt ttggtggaaa ggtaaattag tatttaaagc taaactaaga   1620

gcctctcata cttggaatcc aattcaacaa atgagtatta atgtagataa ccaatttaac   1680

tatgtaccaa gtaatattgg aggtatgaaa attgtatatg aaaaatctca actagcacct   1740

agaaaattat at                                                        1752
```

<210> SEQ ID NO 3
<211> LENGTH: 599
<212> TYPE: PRT
<213> ORGANISM: Raccoon parvovirus
<220> FEATURE:
<221> NAME/KEY: misc_feature
<222> LOCATION: (425)..(425)
<223> OTHER INFORMATION: Xaa can be any naturally occurring amino acid

<400> SEQUENCE: 3

-continued

```
Met Ser Asp Gly Ala Val Gln Pro Asp Gly Gly Gln Pro Ala Val Arg
1               5                   10                  15

Asn Glu Arg Ala Thr Gly Ser Gly Asn Gly Ser Gly Gly Gly Gly Gly
            20                  25                  30

Gly Gly Ser Gly Gly Val Gly Ile Ser Thr Gly Thr Phe Asn Asn Gln
        35                  40                  45

Thr Glu Phe Lys Phe Leu Glu Asn Gly Trp Val Glu Ile Thr Ala Asn
    50                  55                  60

Ser Ser Arg Leu Val His Leu Asn Met Pro Glu Ser Glu Asn Tyr Arg
65                  70                  75                  80

Arg Val Val Val Asn Asn Leu Asp Lys Thr Ala Val Asn Gly Asn Met
                85                  90                  95

Ala Leu Asp Asp Thr His Ala Gln Ile Val Thr Pro Trp Ser Leu Val
            100                 105                 110

Asp Ala Asn Ala Trp Gly Val Trp Phe Asn Pro Gly Asp Trp Gln Leu
        115                 120                 125

Ile Val Asn Thr Met Ser Glu Leu His Leu Val Ser Phe Glu Gln Glu
    130                 135                 140

Ile Phe Asn Val Val Leu Lys Thr Val Ser Glu Ser Ala Thr Gln Pro
145                 150                 155                 160

Pro Thr Lys Val Tyr Asn Asn Asp Leu Thr Ala Ser Leu Met Val Ala
                165                 170                 175

Leu Asp Ser Asn Asn Thr Met Pro Phe Thr Pro Ala Ala Met Arg Ser
            180                 185                 190

Glu Thr Leu Gly Phe Tyr Pro Trp Lys Pro Thr Ile Pro Thr Pro Trp
        195                 200                 205

Arg Tyr Tyr Phe Gln Trp Asp Arg Thr Leu Ile Pro Ser His Thr Gly
    210                 215                 220

Thr Ser Gly Thr Pro Thr Asn Thr Tyr His Gly Thr Asp Pro Asp Asp
225                 230                 235                 240

Val Gln Phe Tyr Thr Ile Glu Asn Ser Val Pro Val His Leu Leu Arg
                245                 250                 255

Thr Gly Asp Glu Phe Ala Thr Gly Thr Phe Phe Phe Asp Cys Lys Pro
            260                 265                 270

Cys Arg Leu Thr His Thr Trp Gln Thr Asn Arg Ala Leu Gly Leu Pro
        275                 280                 285

Pro Phe Leu Asn Ser Leu Pro Gln Ser Glu Gly Asp Thr Asn Phe Gly
    290                 295                 300

Asp Ile Gly Ile Gln Gln Asp Lys Arg Arg Gly Val Thr Gln Met Gly
305                 310                 315                 320

Asn Thr Asn Tyr Ile Thr Glu Ala Thr Ile Met Arg Pro Ala Glu Val
                325                 330                 335

Gly Tyr Ser Ala Pro Tyr Tyr Ser Phe Glu Ala Ser Thr Gln Gly Pro
            340                 345                 350

Phe Lys Thr Pro Ile Ala Ala Gly Arg Gly Gly Ala Gln Thr Asp Glu
        355                 360                 365

Asn Gln Ala Ala Asp Gly Asp Pro Arg Tyr Ala Phe Gly Arg Gln His
    370                 375                 380

Gly Gln Lys Thr Thr Thr Thr Gly Glu Thr Pro Glu Arg Phe Thr Tyr
385                 390                 395                 400

Ile Ala His Gln Asp Thr Gly Arg Tyr Pro Glu Gly Asp Trp Ile Gln
                405                 410                 415

Asn Ile Asn Phe Asn Leu Pro Val Xaa Asn Asp Asn Val Leu Leu Pro
            420                 425                 430
```

-continued

```
Thr Asp Pro Ile Gly Gly Lys Thr Gly Ile Asn Tyr Thr Asn Ile Phe
        435                 440                 445

Asn Thr Tyr Gly Pro Leu Thr Ala Leu Asn Asn Val Pro Pro Val Tyr
    450                 455                 460

Pro Asn Gly Gln Ile Trp Asp Lys Glu Phe Asp Thr Asp Leu Lys Pro
465                 470                 475                 480

Arg Leu His Val Asn Ala Pro Phe Val Cys Gln Asn Asn Cys Pro Gly
                485                 490                 495

Gln Leu Phe Val Lys Val Ala Pro Asn Leu Thr Asn Glu Tyr Asp Pro
            500                 505                 510

Asp Ala Ser Ala Asn Met Ser Arg Ile Val Thr Tyr Ser Asp Phe Trp
        515                 520                 525

Trp Lys Gly Lys Leu Val Phe Lys Ala Lys Leu Arg Ala Ser His Thr
    530                 535                 540

Trp Asn Pro Ile Gln Gln Met Ser Ile Asn Val Asp Asn Gln Phe Asn
545                 550                 555                 560

Tyr Val Pro Ser Asn Ile Gly Gly Met Lys Ile Val Tyr Glu Lys Ser
                565                 570                 575

Gln Leu Ala Pro Arg Lys Leu Tyr His Thr Tyr Tyr Val Phe Met Phe
            580                 585                 590

Ile Thr Tyr Gln Pro Ser Thr
        595


<210> SEQ ID NO 4
<211> LENGTH: 584
<212> TYPE: PRT
<213> ORGANISM: Raccoon parvovirus
<220> FEATURE:
<221> NAME/KEY: misc_feature
<222> LOCATION: (425)..(425)
<223> OTHER INFORMATION: Xaa can be any naturally occurring amino acid

<400> SEQUENCE: 4

Met Ser Asp Gly Ala Val Gln Pro Asp Gly Gly Gln Pro Ala Val Arg
1               5                   10                  15

Asn Glu Arg Ala Thr Gly Ser Gly Asn Gly Ser Gly Gly Gly Gly Gly
            20                  25                  30

Gly Gly Ser Gly Gly Val Gly Ile Ser Thr Gly Thr Phe Asn Asn Gln
        35                  40                  45

Thr Glu Phe Lys Phe Leu Glu Asn Gly Trp Val Glu Ile Thr Ala Asn
    50                  55                  60

Ser Ser Arg Leu Val His Leu Asn Met Pro Glu Ser Glu Asn Tyr Arg
65                  70                  75                  80

Arg Val Val Val Asn Asn Leu Asp Lys Thr Ala Val Asn Gly Asn Met
                85                  90                  95

Ala Leu Asp Asp Thr His Ala Gln Ile Val Thr Pro Trp Ser Leu Val
            100                 105                 110

Asp Ala Asn Ala Trp Gly Val Trp Phe Asn Pro Gly Asp Trp Gln Leu
        115                 120                 125

Ile Val Asn Thr Met Ser Glu Leu His Leu Val Ser Phe Glu Gln Glu
    130                 135                 140

Ile Phe Asn Val Val Leu Lys Thr Val Ser Glu Ser Ala Thr Gln Pro
145                 150                 155                 160

Pro Thr Lys Val Tyr Asn Asn Asp Leu Thr Ala Ser Leu Met Val Ala
                165                 170                 175

Leu Asp Ser Asn Asn Thr Met Pro Phe Thr Pro Ala Ala Met Arg Ser
```

-continued

```
            180                 185                 190

Glu Thr Leu Gly Phe Tyr Pro Trp Lys Pro Thr Ile Pro Thr Pro Trp
        195                 200                 205

Arg Tyr Tyr Phe Gln Trp Asp Arg Thr Leu Ile Pro Ser His Thr Gly
    210                 215                 220

Thr Ser Gly Thr Pro Thr Asn Thr Tyr His Gly Thr Asp Pro Asp Asp
225                 230                 235                 240

Val Gln Phe Tyr Thr Ile Glu Asn Ser Val Pro Val His Leu Leu Arg
                245                 250                 255

Thr Gly Asp Glu Phe Ala Thr Gly Thr Phe Phe Phe Asp Cys Lys Pro
            260                 265                 270

Cys Arg Leu Thr His Thr Trp Gln Thr Asn Arg Ala Leu Gly Leu Pro
        275                 280                 285

Pro Phe Leu Asn Ser Leu Pro Gln Ser Glu Gly Asp Thr Asn Phe Gly
    290                 295                 300

Asp Ile Gly Ile Gln Gln Asp Lys Arg Arg Gly Val Thr Gln Met Gly
305                 310                 315                 320

Asn Thr Asn Tyr Ile Thr Glu Ala Thr Ile Met Arg Pro Ala Glu Val
                325                 330                 335

Gly Tyr Ser Ala Pro Tyr Tyr Ser Phe Glu Ala Ser Thr Gln Gly Pro
            340                 345                 350

Phe Lys Thr Pro Ile Ala Ala Gly Arg Gly Gly Ala Gln Thr Asp Glu
        355                 360                 365

Asn Gln Ala Ala Asp Gly Asp Pro Arg Tyr Ala Phe Gly Arg Gln His
    370                 375                 380

Gly Gln Lys Thr Thr Thr Thr Gly Glu Thr Pro Glu Arg Phe Thr Tyr
385                 390                 395                 400

Ile Ala His Gln Asp Thr Gly Arg Tyr Pro Glu Gly Asp Trp Ile Gln
                405                 410                 415

Asn Ile Asn Phe Asn Leu Pro Val Xaa Asn Asp Asn Val Leu Leu Pro
            420                 425                 430

Thr Asp Pro Ile Gly Gly Lys Thr Gly Ile Asn Tyr Thr Asn Ile Phe
        435                 440                 445

Asn Thr Tyr Gly Pro Leu Thr Ala Leu Asn Asn Val Pro Pro Val Tyr
    450                 455                 460

Pro Asn Gly Gln Ile Trp Asp Lys Glu Phe Asp Thr Asp Leu Lys Pro
465                 470                 475                 480

Arg Leu His Val Asn Ala Pro Phe Val Cys Gln Asn Asn Cys Pro Gly
                485                 490                 495

Gln Leu Phe Val Lys Val Ala Pro Asn Leu Thr Asn Glu Tyr Asp Pro
            500                 505                 510

Asp Ala Ser Ala Asn Met Ser Arg Ile Val Thr Tyr Ser Asp Phe Trp
        515                 520                 525

Trp Lys Gly Lys Leu Val Phe Lys Ala Lys Leu Arg Ala Ser His Thr
    530                 535                 540

Trp Asn Pro Ile Gln Gln Met Ser Ile Asn Val Asp Asn Gln Phe Asn
545                 550                 555                 560

Tyr Val Pro Ser Asn Ile Gly Gly Met Lys Ile Val Tyr Glu Lys Ser
                565                 570                 575
```

-continued

```
Gln Leu Ala Pro Arg Lys Leu Tyr
            580


<210> SEQ ID NO 5
<211> LENGTH: 557
<212> TYPE: DNA
<213> ORGANISM: Raccoon parvovirus

<400> SEQUENCE: 5

tcaggaagat atccagaagg agattggatt caaaatatta actttaacct tcctgtaaca      60

aatgataatg tattgctacc aacagatcca attggaggta aaacaggaat taactatact     120

aatatattta atacttatgg tcctttaact gcattaaata atgtaccacc agtttatcca     180

aatggtcaaa tttgggataa agaatttgat actgacttaa aaccaagact tcatgtaaat     240

gcaccatttg tttgtcaaaa taattgtcct ggtcaattat ttgtaaaagt tgcgcctaat     300

ttaacaaatg aatatgatcc tgatgcatct gctaatatgt caagaattgt aacttactca     360

gatttttggt ggaaaggtaa attagtattt aaagctaaac taagagcctc tcatacttgg     420

aatccaattc aacaaatgag tattaatgta gataaccaat ttaactatgt accaagtaat     480

attggaggta tgaaaattgt atagaaaaat ctcaactagc acctagaaaa ttatattaac     540

aacttagcta gtcttat                                                    557


<210> SEQ ID NO 6
<211> LENGTH: 565
<212> TYPE: DNA
<213> ORGANISM: Raccoon parvovirus

<400> SEQUENCE: 6

ggtcaggaag atatccagaa ggagattgga ttcaaaatat taactttagc cttccggtgg      60

caaatgataa tgtattgctg ccaacaggtc caattggagg taaaacagga attaactata     120

ctaatatatt taatacgtat ggtcctttaa ctgcattaaa taatgtacca ccagtttatc     180

caaatggtca aatttgggat aaagaatttg atactgactt aaaaccaaga cttcatgtaa     240

atgcaccatt tgtttgtcaa aataattgtc ctggtcaatt atttgtaaaa gttgcgccta     300

atttaacaaa tgaatatgat cctgatgcat ctgctaatat gtcaagaatt gtaacttact     360

cagatttttg gtggaaaggt aaattagtat ttaaagctaa actaagagcc tctcatactt     420

ggaatccaat tcaacaaatg agtattaatg tagataacca atttaactat gtaccaagta     480

atattggagg tatgaaaatt gtatagaaaa attctcaaac tagcacctag aaaattatat     540

aacaacttta cttctggtgg gcggg                                           565


<210> SEQ ID NO 7
<211> LENGTH: 556
<212> TYPE: DNA
<213> ORGANISM: Raccoon parvovirus

<400> SEQUENCE: 7

tcaggaagat atccagaagg agattggatt caaaatatta actttaacct tcctgtaaca      60

aatgataatg tattgctacc aacagatcca attggaggta aaacaggaat taactatact     120

aatatattta atacttatgg tcctttaact gcattaaata atgtaccacc agtttatcca     180

aatggtcaaa tttgggataa agaatttgat actgacttaa aaccaagact tcatgtaaat     240

gcaccatttg tttgtcaaaa taattgtcct ggtcaattat ttgtaaaagt tgcgcctaat     300
```

-continued

| | |
|---|---|
| ttaacaaatg aatatgatcc tgatgcatct gctaatatgt caagaattgt aacttactca | 360 |
| gatttttggt ggaaaggtaa attagtattt aaagctaaac taagagcctc tcatacttgg | 420 |
| aatccaattc aacaaatgag tattaatgta gataaccaat ttaactatgt accaagtaat | 480 |
| attggaggta gaaaattgta tagaaaaatc tcaactagca cctagaaaat tatattaaca | 540 |
| acttagctag gcgtat | 556 |

ISOLATION OF A VIRUS RELATED TO CANINE PARVOVIRUS-2 FROM A RACCOON

SEQUENCE LISTING

This application includes as the Sequence Listing the complete contents of the accompanying text file "PCT Sequence Listing_ST25.txt", created Oct. 14, 2010, containing 18,268 bytes, hereby incorporated by reference.

DESCRIPTION

BACKGROUND OF THE INVENTION

1. Field of the Invention

The invention generally relates to improved vaccines against canine parvovirus-like viruses. In particular, the invention provides vaccines suitable for puppies which are based on a novel parvovirus isolated from a raccoon.

2. Background of the Invention

Canine parvovirus (CPV) is primarily an enteric pathogen that infects dogs, especially young dogs. Parvovirus infection is characterized by acute diarrhea, fever and leukopenia in dogs and puppies more than 4 to 5 weeks old, and myocardial disease in younger puppies. The mortality rate from the disease in unvaccinated dogs is very high. While vaccines against CPV are available, because CPV is a single-stranded DNA virus and has an extreme ability to mutate, the virus shows a remarkable ability to vary antigenically (Parrish and Kawaoka 2005) and thereby elude the immune protection afforded by vaccines. Thus, constant monitoring of the antigenic type and genotype of circulating viruses, and adjustment of vaccine components accordingly, is necessary.

Newborn puppies acquire immunities against diseases such as CPV infection by nursing from their mother, especially during the first two days of life. A puppy that nurses takes in colostrum in the milk that is first produced and antibodies in the colostrum are passed to the puppy. For dogs and many other mammals as well, the immunity given by the colostrum loses its affect sometime around the fifth week of age.

A particular challenge when vaccinating puppies is to administer vaccines according to a time frame that provides protection which overlaps the protection provided by maternal antibodies and begins as maternal antibodies wane. Currently, vaccine regimens for puppies typically begin at about 6 weeks of age and boosters are given about every 3 weeks thereafter, e.g. at 9, 12 and 15 weeks. However, in order for this regimen to provide full protection, the first vaccine dose must immediately elicit a protective immune response. This is completely unrealistic due to the immaturity of the puppy's immune system and the time period required to mount an immune response. Full protection usually does not develop until the entire course of vaccinations is given. The age-based mortality due to CPV is depicted in FIG. 1, which shows that maximum mortality due to CPV occurs before vaccine protocols can be completed.

A simple answer might be to begin the vaccination program even earlier, e.g. at 2-3 weeks. However, this would be futile because, for puppies whose mothers have been vaccinated with or otherwise exposed to a viral strain with the same antigenic determinants, maternal antibodies passed to the puppy would neutralize viruses in the vaccine, thereby preventing the puppy's own immune system from responding to the virus.

Another challenge in veterinary medicine is the treatment of cancer, e.g., in dogs. There are many limitations in the existing tools for cancer therapy, especially for geriatric dogs. The administration of oncolytic parvoviruses to kill cancer cells shows great promise as an effective cancer treatment (Rommelaere et al, *Cytokine & Growth Factor Reviews* 21:185-195, 2010; and U.S. Pat. No. 7,179,456 to Rommelaere et al, the complete contents of which are herein incorporated by reference) and might be applied to canines. However, the existence of pre-existing antibodies to parvoviruses (e.g. as a result of vaccination) would render this method ineffective, since the parvovirus would be neutralized by the existing antibodies. In addition, gene therapy in dogs is rarely undertaken at present but would be a promising method for treating several disorders, if suitable nucleic acid vectors are identified.

The prior art has thus far failed to provide solutions to these problems.

SUMMARY OF THE INVENTION

The present invention is based on the discovery of novel parvoviruses (isolated from raccoons in the USA). Analyses of nucleotide and amino acid sequences showed that the viruses represent a unique variant of canine parvovirus type 2 (CPV-2). This new CPV-2, denominated "AR08071304" (and referred to herein as raccoon parvovirus, "RPV", "08071304", and "Parvovirus-2 (Raccoon)" etc.) is useful as a component of vaccines against canine parvovirus. In particular, the variant is useful as a component of vaccines for very young dogs, e.g. puppies who are still nursing or who are in the process of being weaned, and thus solves the problems of how to provide adequate puppy vaccine protocols. This raccoon parvovirus will not be completely neutralized by existing canine parvovirus-2 antibodies in dogs. In addition, this raccoon parvovirus can be used as an oncolytic agent and as a vector (carrier, vehicle) for gene therapy, due to the lack of neutralization by pre-existing antibodies in a recipient or host organism, e.g. a dog.

The variant virus has close homology to the predominant CPV-2 viruses currently in circulation. Thus, administration of a vaccine containing the new variant is likely to result in an immune response that also affords protection against known circulating CPV-2 viruses. However, there are some antigenic differences between the new isolate and known CPV-2 viruses to which a mother dog is likely to have been exposed (e.g. via a vaccine preparation or prior CPV exposure). In particular, amino acid residue 232 of the variant capsid protein, VP-2 is Thr (encoded by ACA) and amino acid residue 300 is Asp (encoded by GAT). These differences in sequence are sufficient to result in a unique immunoreactive profile for the variant. Therefore, maternal antibodies passed to a puppy (e.g. from a previously vaccinated/exposed mother) are not likely to completely inactivate the new virus when it is administered to a puppy as a vaccine. As a result, an immune response by the puppy's own immune system will be elicited upon exposure to the RPV of the present invention via vaccination, and the immune response is likely to be broadly protective against currently circulating CPV's in general. Moreover, this raccoon parvovirus appears to be a natural chimera of carnivore parvoviruses. Although the nucleotide sequence encoding the RPV VP-2 protein has the highest total homology score (3309) with canine parvovirus-2a (CPV-15), it also has high homology with feline panleukopaenia, previously isolated raccoon parvoviruses, and mink enteritis virus. This type of chimeric sequence has not been observed previously in canine or feline parvovirus sequences, although similar parvoviruses now appear to be circulating in raccoon populations in the USA (see Examples section below). This RPV will provide broad immune protection in several carnivore species and is thus suitable for use as a broad spectrum parvovirus vaccine. Under rare, unusual circumstances, a dog or cat might succumb to infection with a heterologus live, non-attenuated carnivore parvovirus; however, the benefits of using the RPV of the invention as described herein far outweigh this minimal risk.

Although the present invention is not premised on any evolutionary model or theory, one interesting interpretation of the genetic data disclosed herein is that the RPV of the present invention may represent the ancestor of present-day canine and feline parvoviruses. There is an ongoing debate in virology community concerning the origin of parvovirus-2 of dogs, and the RPV of the invention would, within the confines of this theory, be a "living fossil" of canine parvovirus-2. In any case, the RPV described herein encodes a unique VP-2 protein, which comprises a mosaic of feline and canine parvovirus amino acid sequences. Thus the RPV of the present invention is a candidate for being the "ancestor" of both feline and canine parvoviruses, i.e., these newer carnivore parvoviruses having originated from this RPV. Alternatively, the RPV of the present invention may represent a chimeric intermediate at the "intersection" of parvovirus evolution. In any case, this RPV provides an avenue for cross-immunization against heterologous parvoviruses that is otherwise not presently available with any of the more species-specialized canine and feline parvoviruses. Moreover, the RPV of the invention is weakly agglutinating for porcine erythrocytes (transferrin); does not share some critical epitopes (e.g., amino acid residue 300 of the VP-2 protein sequence); and grows poorly in feline kidney cell lines (see Examples below). Taken together, these indications are consistent with a virus that either predates or is an early intermediate in the evolutionary cascade of canine and feline parvoviruses.

The invention provides a parvovirus comprising the characteristics of the Parvovirus-2 (Raccoon) of ATCC NO. PTA-11400, deposited at the American Type Culture Collection, 10801 University Blvd, Manassas, Va., on Oct. 7, 2010.

In addition, the invention provides vaccines comprising a parvovirus comprising the characteristics of the Parvovirus-2 (Raccoon) having the ATCC NO. PTA-11400. In one embodiment, the vaccine further comprises one or more antigenic components selected from the group consisting of canine distemper virus (CDV), canine adenovirus type 2, canine parainfluenza virus, canine corona virus, canine herpes virus, canine rotavirus, one or more *Leptospira* serovars, and a canine parvovirus-2 in which the amino acid at position 232 of VP-2 protein is not Thr and the amino acid at position 300 of VP-2 protein is not Asp. In some embodiments, the one or more *Leptospira* serovars is selected from the group consisting of *Leptospira interrogans* serovar *canicolar, Leptospira interrogans* serovar *icterohaemorrhagiae, Leptospira interrogans* serovar *Pomona*, and *Leptospira kirschneri* serovar *grippotyphosa.*

The invention also provides isolated nucleic acids comprising the nucleotide sequence SEQ ID NO: 1, or a portion of SEQ ID NO: 1; wherein the portion of SEQ ID NO: 1 encodes an antigenic region of a VP-2 protein comprising amino acid residue 232 of SEQ ID NO: 3, amino acid residue 300 of SEQ ID NO: 3 or both amino acid residue 232 and amino acid residue 300 of SEQ ID NO: 3. In other embodiments, the invention provides immununogenic compositions comprising this nucleic acid, wherein the nucleic acid is present in a killed or attenuated parvovirus virion or low passage raccoon parvovirus (RPV). In some embodiments, the killed parvovirus virion comprises the characteristics of Parvovirus-2 (Raccoon) having the ATCC NO. PTA-11400. In other embodiments, the attenuated parvovirus virion is present in a solid carrier suitable for supralingual dissolution. In yet other embodiments, the immununogenic composition is suitable for subcutaneous administration.

The invention also provides a method of eliciting an immune response in an animal against parvovirus infection. The method comprises the step of administering to the animal an immunogenic composition comprising a nucleic acid comprising the nucleotide sequence SEQ ID NO: 1, or a portion of SEQ ID NO: 1; wherein said portion of SEQ ID NO: 1 encodes an antigenic region of a VP-2 protein comprising amino acid residue 232 of SEQ ID NO: 3, amino acid residue 300 of SEQ ID NO: 3 or both amino acid residue 232 and amino acid residue 300 of SEQ ID NO: 3. In some embodiments, the nucleic acid is present in a killed or attenuated parvovirus virion or low passage RPV in a killed or attenuated parvovirus virion. In some embodiments, the killed parvovirus virion comprises the characteristics of Parvovirus-2(Raccoon) having the ATCC NO. PTA-11400. In some embodiments, the attenuated parvovirus virion is present in a solid carrier suitable for supralingual dissolution, and in some embodiments, the animal is a puppy. In other embodiments, the immununogenic composition is suitable for subcutaneous administration.

The invention further provides a substantially purified parvovirus VP-2 protein that has a threonine residue at amino acid position 232 and an aspartic acid residue at amino acid position 300; or an antigenic fragment thereof, wherein said antigenic fragment comprises at least a portion of said VP-2 protein that has: a threonine residue at amino acid position 232; or an aspartic acid residue at amino acid position 300; or both a threonine residue at amino acid position 232 and an aspartic acid residue at amino acid position 300. In some embodiments, the substantially purified parvovirus VP-2 protein comprises amino acid sequence SEQ ID NO: 3.

The invention also provides expression vectors comprising a nucleotide sequence encoding the amino acid sequence of SEQ ID NO: 3, or a portion of SEQ ID NO: 3; wherein said portion of SEQ ID NO: 3 is an antigenic region of a VP-2 protein comprising amino acid residue 232 of SEQ ID NO: 3, amino acid residue 300 of SEQ ID NO: 3 or both amino acid residue 232 and amino acid residue 300 of SEQ ID NO: 3. In some embodiments, the expression vector is a recombinant viral expression vector. In other embodiments, the recombinant viral expression vector is a canarypox viral expression vector.

The invention also provides methods of killing tumor cells in a mammal. The methods comprise the step of administering to the mammal a composition comprising a parvovirus comprising the characteristics of the Parvovirus-2 (Raccoon) of ATCC NO. PTA-11400, in a quantity sufficient to infect and kill said tumor cells in the mammal. In some embodiments, the mammal is a dog that is seropositive for canine parvovirus-2. In other embodiments, the method is carried out by a route of administration selected from the group consisting of intravenous and intratumoral. In yet other embodiments, the parvovirus is a low passage parvovirus.

BRIEF DESCRIPTION OF THE DRAWINGS

FIGS. 2A and B. Nucleic acid sequences encoding the VP-2 proteins of the new AR08071304 CPV-2 variant. A, the longer version of the nucleotide sequence (SEQ ID NO: 1) which encodes a 599 amino acid protein. The internal stop codon located at nucleotides 1753-1755 is shown in bold and underlined. B, the shorter version of the nucleotide sequence (SEQ ID NO: 2) which encodes a 584 amino acid protein. In both A and B, the nucleotides encoding Thr at position 232 (nts 694-696) and the nucleotides encoding Asp at position 300 (nts 898-900) are underlined.

FIGS. 3A and B. Amino acid sequence of the VP-2 protein of the new AR08071304 CPV-2 variant. A. (SEQ ID NO: 3), is the longer version of the protein when all 599 encoded amino acids are translated; B, (SEQ ID NO: 4), is the shorter version of the protein when termination occurs at the stop condon. Amino acid positions 232 and 300, which are Thr and Asp, respectively in both proteins, are boxed.

FIG. 4A-C. Schematics of: A, raccoon parvovirus (RPV) DNA; B, RPV open reading frame arrangement; C, binding of RPV to eukaryotic cells.

FIG. 7. Amino acids at critical epitopes in VP-2 protein of the newly isolated raccoon parvovirus.

DETAILED DESCRIPTION

Figure 1:
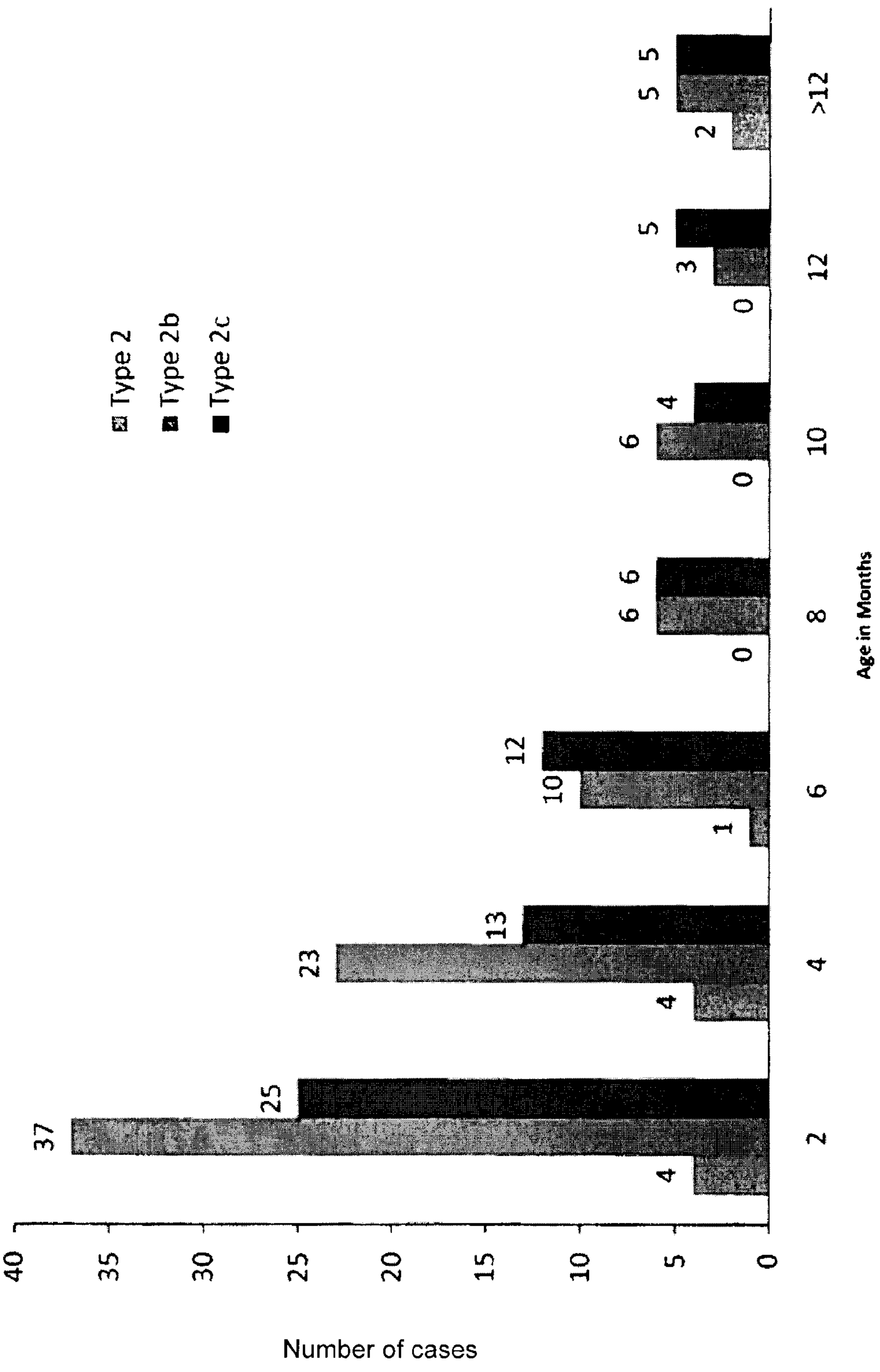
FIG. 1. Distribution of CPV-2 genotypes and number of fatal cases of CPV infection with respect to age of dog.

The invention provides vaccine and virotherapy preparations comprising attenuated forms of a novel parvovirus variant isolated from an infected raccoon. While the vaccine preparations are suitable for administration to a wide variety of carnivores (e.g. dogs, cats, mink, raccoon, members of canidae, procyonidea, mustelidae, and viveridae etc.), they are particularly useful for administration to very young dogs (puppies). This is because the new variant differs enough from CPV variants that are used in current vaccines so as to make it unlikely that maternal antibodies (developed in response to vaccine administration and passed to the puppies while nursing) would recognize and inactivate the virus. Similarly, for other applications in dogs, including adult dogs (e.g. as a treatment for cancer and as a gene therapy vector) the RPV will bypass the preexisting antibodies from previous vaccinations, and hence evade immediate immune clearance. Notably, in the VP-2 protein of the raccoon isolate amino acid residue 232 is Thr (encoded by ACA) and residue 300 is Asp (encoded by GAT). These two amino acid residues in the RPV are thus distinct from those of the VP-2 proteins of all other known CPV isolates and may be responsible for the unique properties (e.g. antibody reactivity, see Examples below) of this RPV. Due to attenuation, the virus will not cause disease in vaccine recipients. On the other hand, the new isolate is similar enough to viruses which are currently in circulation (e.g. the amino acid sequence identity is ~99% for the VP-2 protein) that is it likely that administration of the virus to a young animal would result in the production of antibodies, at least some of which would cross react with known circulating viruses, and thus afford protection against those viruses to the vaccinated young animal.

A nucleic acid sequence described herein (SEQ ID NO: 1) contains an internal stop codon at nucleotides 1753-1755 (see FIG. 2A). The VP-2 protein translated therefrom thus has two different forms. One form, shown in FIG. 3A (SEQ ID NO 3) results from readthrough ("leakiness") of the stop codon and is thus longer (599 amino acids) than the second form, which is shown in FIG. 3B, and which terminates at the stop codon. The second form of the protein contains only 584 amino acids (SEQ ID NO: 4). In the first, longer form of VP-2 the stop codon is not translated but is "skipped", resulting in the 599 amino acid protein. The term "VP-2" protein as used herein encompasses both the first longer form of VP-2 and the second, shorter form of VP-2, and both forms of the protein may be used in the practice of the invention. These two forms of the protein can be detected using Western blots. In addition, both nucleic acid sequences (SEQ ID NOS: 1 and 2) may be used in the practice of the present invention, e.g. either or both of the sequences may be used in a vaccine preparation, in a vector, etc. In some embodiments, the amino acid sequence of SEQ ID NO: 3 is encoded by the nucleotide sequence of SEQ ID NO: 1. In other embodiments, the amino acid sequence of SEQ ID NO: 4 is encoded by SEQ ID NO: 2. In yet other embodiments of the invention, SEQ ID NO: 1 may be modified by elimination (deletion) of the stop codon (e.g. by genetic engineering) so that the amino acid sequence of SEQ ID NO: 3 is translated therefrom.

This novel RPV also serves as a model for proper boosting of other animal and human infections. For example in human influenza (H1N1) based on available information, vaccine response varies depending on the existence of pre-existing antibodies. If a person has pre existing antibodies, the titer does not go up but the affinity of the antibodies does increase. If a person does not have a pre-existing titer, then the person does respond with development of neutralizing protective immunity.

The new isolate was deposited at the American Type Culture Collection in Manassas, Va., on Oct. 7, 2010, as Parvovirus-2 (Raccoon), on behalf of Oklahoma State University, (acknowledgement from the ATCC of receipt was received on Oct. 12, 2010), and assigned ATCC Deposit No. PTA-11400. The invention also provides an isolated parvovirus comprising the characteristics of ATCC Deposit No. PTA-11400, and progeny thereof. The invention further encompasses killed or attenuated parvoviruses comprising the characteristics of ATCC Deposit No. PTA-11400, deposited on Oct. 7, 2010 and progeny of the attenuated parvoviruses, as well as vaccines and immunogenic compositions comprising the same.

The invention also provides other RPV's isolated in Illinois and propagated in CRFK. (10071199-A and 10071199-C), the partial sequences of which are given in the Examples section. Thus, the invention also encompasses raccoon parvoviruses that are circulating in the USA (e.g. in Arkansas and Illinois), the common feature of which is that they do not react with the canine parvovirus monoclonal antibody (MoAb) 3B10, the MoAb that is most commonly used for diagnostics. 3B10 is specific for amino acid position 300 of VP-2, which is usually glycine. Thus, these RPV have a mutation at amino acid 300 of VP-2 that is included within the foot-print of this MoAb and prevents it from recognizing the proteins. Otherwise, these viruses have about 98% homology with the VP-2 of other carnivore parvoviruses-2. However, it is well-established that even a small number of mutations at critical locations can have a large impact on the properties of a virus (e.g. see Qu e al, 2005, where mutations in two critical amino acid residues of coronavirus spike protein, which altered its tropism, are described.)

Phylogenetic studies of this virus (e.g. see Examples 1 and 5) have shown that this RPV [Parvovirus-2 (Raccoon)] is closely related to, and in fact may be, a variant of canine CPV-2. As such, domestic adult dogs may also be susceptible to the virus and would likely benefit from receiving vaccines which include this variant.

Transmission of the newly isolated parvovirus from raccoons to domestic pets such as dogs, and also to other wildlife is likely to occur due to raccoon behavioral characteristics. For example, raccoons are highly intelligent and very quick to adapt to new food sources. They are omnivorous, eating a wide rage of plants and animals, depending upon season and availability. Due to their ready integration into and adaption to urban areas, raccoons commonly interact with and make close contact with domestic dogs and cats. Raccoons have excellent prehensile abilities and readily learn, e.g. to open containers, to locate and open stored animal food, etc. Due to this behavior, they are potentially able to transmit parvovirus to domestic carnivores. Raccoons also interact with other wildlife such as skunks and there is thus a potential for interspecies interaction and transmission of parvoviruses as well. Thus, adult dogs and other domestic pets would thus benefit from receiving vaccines which included the raccoon virus described herein, even if they have previously been vaccinated with another parvovirus vaccine; and other species, whether domesticated or not, would also benefit from receiving such vaccines. The benefits could be two-fold: 1) vaccination would provide immunity to infection with this particular CPV; and 2) this CPV is similar enough to other parvoviruses (e.g. about 99% homologous to other carnivore parvoviruses) that is would likely also elicit and boost at least some immunity against them.

In some embodiments, the vaccines and immunogenic compositions of the invention are monovalent in nature, i.e. that contain a single agent which is the parvovirus isolate described herein (e.g. with the characteristics of Parvovirus-2 (Raccoon), ATCC Deposit No. PTA-11400 deposited on Oct. 7, 2010), or an attenuated or killed form of the isolate described herein, or progeny of any of these. In other embodiments, the vaccines and immunogenic compositions are polyvalent, i.e. they contain a plurality of antigenic agents, one of which is the isolate of the present invention. Exemplary additional components of the multivalent compositions include but are not limited to one or more of a canine distemper viruses (CDV), canine adenovirus type 2, canine parainfluenza virus, canine corona virus, canine herpes virus, canine rotavirus, one or more *Leptospira* serovars, and a canine parvovirus-2 which differs in sequence of the VP-2 gene, i.e. in which the amino acid at position 232 of the VP-2 protein is not Thr and/or the amino acid at position 300 of the VP-2 protein is not Asp; or in which the codon encoding Thr at amino acid position 232 of the VP-2 protein is not ACA, and/or the codon encoding Asp at amino acid position 300 of the VP-2 is not GAT. Exemplary CDVs include but are not limited to those described in U.S. patent application Ser. No. 12/696,983 (Kapil), published as US2010/0196420, the complete contents of which are hereby incorporated by reference. Exemplary *Leptospira* serovars include but are not limited to *Leptospira interrogans* serovar *canicolar, Leptospira interrogans* serovar *icterohaemorrhagiae, Leptospira interrogans* serovar *pomona*, and *Leptospira kirschneri* serovar *grippotyphosa*. Further, the isolate of the invention may be combined with a plurality of different antigens e.g. those of known multivalent vaccines such as Galaxy® DA2PPV, or Nobivac DA2PPv+L4, etc.

In a particular embodiment, the recipient of a vaccine of the invention is a juvenile animal (e.g. a puppy) and the mode of administration is via a "puppy lollipop". Puppy lollipops for use in administering vaccine compositions to young dogs (or the young of other species) are described in detail in co-pending PCT patent application no. PCT/US2010/042142 to Kapil et al., filed Jul. 15, 2010, the complete contents of which is hereby incorporated by reference. Briefly, a puppy lollipop or similar device is used to deliver the vaccine to the dorsal side of the tongue, i.e. supralingually. In particular, the vaccine preparation is administered in a manner that delivers the vaccine at or near the basal cells of the tongue. Basal cells are infected by the attenuated parvovirus in the vaccine, and an antigen depot (e.g. a reservoir of virus) is established which gradually, over time and from a very young age, releases attenuated parvovirus within the puppy. This method takes advantage of the fact that the tongue is relatively immunologically privileged (devoid of immune response). The vaccine may, for example, be included in a hand-held "puppy lollipop" that is administered supralingually by a caregiver, e.g. by holding a stick, string or other delivery vehicle attached to a solid vaccine formulation which is placed in the puppy's mouth. The solid formulation includes a solid, inert carrier; with the parvovirus dispersed or distributed throughout the solid carrier, and the innate suckling response by the puppy gradually dissolves the carrier and the parvovirus is released to the tongue.

In one embodiment, the invention comprises nucleic acids with a nucleotide sequence encoding the VP-2 protein of the RPV, such as that which is set forth in SEQ ID NO: 1, or alternatively SEQ ID NO: 2 (see FIGS. 2A and B), or portions of that nucleotide sequence that encode antigenic regions or epitopes sufficient to elicit an immune response to the RPV in a vaccine recipient, and vaccines comprising the same. In particular, such nucleic acid sequences will include one or both of the codons which encode positions 232 and 300 of the VP-2 protein. Those codons are ACA and GAT, respectively, encoding Thr and Asp, respectively. In another embodiment, the invention comprises nucleic acids with a nucleotide sequence encoding a VP-2 protein comprising the amino acid sequence as set forth in SEQ ID NO: 3 (or alternatively, SEQ ID NO: 4, which is encompassed by SEQ ID NO: 3, see FIGS. 3A and B) or portions of the amino acid sequence set forth in SEQ ID NO: 3 which include antigenic regions or epitopes sufficient to elicit an immune response to the antigenic regions or epitopes in a vaccine recipient, and vaccines comprising the same. In particular, such proteins or portions thereof will include one or both of amino acid residues 232 and 300 of the RPV VP-2 protein, which are Thr and Asp, respectively. Variants and/or derivatives of such sequences, as described herein, and vaccine preparations which include the variants and/or derivatives, are also encompassed by the invention. For example, those of skill in the art will recognize that, due to the redundancy of the genetic code, sequences other than SEQ ID NO: 1 may be utilized to encode the amino acid sequence set forth in SEQ ID NO: 3. In addition, while the nucleotide sequence set forth in SEQ ID NO: 1 represents single-strand (ss)DNA, the invention also includes corresponding double-strand (ds) DNA, complementary DNA, and RNA of any form (e.g. mRNA, RNA/DNA hybrids, etc.) that is based on, derived from or that complements these sequences. Such sequences may be either sense or antisense sequences. Further, sequences which display at least about 50% homology, preferably about 60%, more preferably about 70, 80, or 90% homology, or even about 95, 96, 97, 98 or 99% or greater homology to SEQ ID NO: 1 are also contemplated for use in the vaccines, so long as the sequence encodes one or both of amino acid residues 232 and 300 as Thr and Asp, respectively. Such sequences may differ, for example, by containing alternate codons that encode the same amino acid at one or more positions.

In addition, portions of these sequences which encode antigenic regions or epitopes of the AR08071304 VP-2 protein are also contemplated. In particular, nucleotide sequences encompassing codons which encode one or both of amino acid residues 232 and 300 as Thr and Asp, respectively, are contemplated. In one embodiment, the codon encoding amino acid residue 232 as Thr is ACA and the codon encoding residue 300 as Asp is GAT. In addition, sequences which encode amino acid sequences displaying 70%, or more preferably about 80, 90, or 95% or even greater identity (e.g. 96, 97, 98 or 99% identity) to SEQ ID NO: 3, so long as the sequence encodes one or both of amino acid residues 232 and 300 as Thr and Asp, respectively, or variants and/or derivatives thereof, including shorter antigenic regions or epitopes, are also included. Such variants and/or derivatives of SEQ ID NO: 3 and/or antigenic regions or epitopes thereof may vary, for example, by containing conservative or non-conservative amino acid substitutions, or deletions (especially amino or carboxy terminal deletions), or various insertions, etc., so long as the resulting protein/peptide is antigenic and elicits an immune response in a vaccine recipient. Such antigenic regions or epitopes are preferably at least about 10 amino acids in length and encompass one or more of amino acid positions 232 and 300, with reference to amino acid residue numbering in the VP-2 protein as depicted in FIG. 3, which are Thr and Asp respectively. An antigenic region may, however, encompass the entire AR08071304 VP-2 gene/protein.

Further, nucleic acid sequences which hybridize to sequences disclosed herein (or to portions of those sequences) under stringent conditions (especially conditions of high stringency) are also contemplated, so long as the sequence encodes one or both of amino acid residues 232 and 300 as Thr and Asp, respectively. Stringent conditions refer to hybridization conditions which allow a nucleic acid sequence to hybridize to a particular sequence. In general, high stringent conditions refer to the hybridization conditions which allow a nucleic acid sequence of at least 50 nucleotides and preferably about 200 or more nucleotides to hybridize to a particular sequence at about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. These conditions allow the detection of sequences having about 90% or more sequence identity. In general, lower stringent conditions refer to the hybridization conditions which allow a nucleic acid sequence of at least 50 nucleotides and preferably about 200 or more nucleotides to hybridize to a particular sequence at about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. These conditions allow the detection of sequences having up to 50% sequence identity. The person skilled in the art will be able to modify these hybridization conditions in order to identify sequences varying in identity between 50% and 90%.

The invention thus also provides various types of recombinant and/or expression vectors that contain and express the nucleic acid sequences disclosed herein (or portions thereof that encode antigenic peptides and/or polypeptides). Such vectors may be used in vaccine preparations, or may serve other purposes such as for manipulation of the disclosed sequence in a laboratory setting. Examples of such vectors and expression systems include but are not limited to: various bacterial (e.g. *Escherichia coli*) or probiotic-based (e.g. *Lactobacillus*) expression vectors; various recombinant viral vectors such as adenoviral vectors, baculovirus, canarypox vectors, etc.; *Pichia*, and yeast expression systems, etc. Such recombinant vectors and expression systems may be utilized, for example, in vaccine preparations, or, alternatively, for other purposes such as for laboratory manipulation of the sequences, or for research or diagnostic purposes.

The invention also contemplates chimeric proteins and genes encoding the same, such proteins comprising the VP-2 protein of the RPV of the invention, or antigenic regions or epitopes thereof. In certain embodiments, such epitopes are of a size in the range of from at least about 5 to about 20 or more amino acids. Such chimeric proteins (or nucleic acid sequences that encode them) may include other useful amino acid sequences, such as adjuvants, other proteins that are vaccine targets e.g. from other organisms that cause disease in carnivores, especially canids, etc. Nucleic acids encoding such proteins may include linker or spacer sequences e.g. between antigenic regions or epitopes. Also included are recombinant and/or expression vectors that encode and/or expresse such chimeric (or fusion) proteins.

Several methods of making vaccines suitable for vaccination against parvovirus are known in the art. See, for example, U.S. Pat. Nos. 4,193,990 and 4,193,991 to Appel et al., U.S. Pat. No. 4,303,645 to Carmichael et al., U.S. Pat. No. 4,971,793 to Wood et al.; U.S. Pat. No. 5,882,652 to Valdes et al., and U.S. Pat. No. 5,885,585 to Parrish et al., each of which offers variations of suitable vaccine-formulating strategies. The complete contents of each of these patents are hereby incorporated by reference. Generally, to manufacture a vaccine, a viral vector containing the described nucleic acid sequences (e.g. ssDNA naturally occurring within a virus, or ssDNA or other equivalent form genetically engineered into a non-native viral vector (e.g. dsDNA, ss or dsRNA, RNA-DNA hybrids, etc.) will be employed. Examples include RPV (or other) viruses that are "killed", inactivated or otherwise attenuated so as to not cause severe disease symptoms in the animal to which it is administered, together with a suitable physiological carrier. Preferably, no disease symptoms will occur as a result of administration. However, those of skill in the art will recognize that many effective vaccine compositions cause some discomfort or relatively minor distress upon or after administration. However, the benefits of being protected against full-blown disease far outweigh this possibility. As an alternative, a heterotypic virus that does not naturally infect or that does not normally cause disease in the animal being vaccinated may be utilized. Examples of ways of inactivating the antigens of the present invention (e.g., the RPV of the present invention) include, but are not limited to, heat, formaldehyde, formalin, biethylene amine, radiation, and beta-propiolactone treatment.

Other suitable vaccine components, e.g. pharmacologically acceptable carriers, are well-known to those of skill in the art, as is the preparation of such compositions for use as vaccines. Typically, such compositions are prepared either as liquid solutions or suspensions, however solid forms such as tablets, pills, powders and the like are also contemplated. Solid forms suitable for solution in, or suspension in, liquids prior to administration, or for dissolution in the mouth, may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of the translatable nucleic acid in the formulations may vary. However, in general, the amount will be from about 1-99%. The compositions may further comprise an adjuvant, suitable examples of which include but are not limited to Seppic, Quil A, Alhydrogel, etc.

Generally, for administration as a vaccine, a nucleic acid will be included in a virus or virion particle and the entire particle will be a vaccine component. As will be understood by those of skill in the art, when the vaccine contains virions (such as the RPV of the present invention) they will be inactivated (killed) or attenuated, i.e. obtained after several passages of the virus in cell culture so that particles do not cause symptoms of disease, or cause only mild, non-life threatening symptoms. Those of skill in the art will also recognize that other methods of attenuating viruses exist, and any of these may be used in the practice of the present invention to develop a suitable form of the variant virus disclosed herein. For example, various mutations that interfere with virus toxicity, ability to reproduce, etc. may be introduced.

Alternatively, the nucleotide sequence presented in SEQ ID NO: 1 (or segments thereof that encode antigenic regions or epitopes as described herein, for example SEQ ID NO: 2)) may be delivered in a heterologous vector such as a different virus (e.g. a virus that does not cause disease in the vaccine recipient species), or another type of construct that is designed to result in expression of the encoded protein in the vaccine recipient, without causing symptoms of disease. Examples of such viruses include but are not limited to feline panleukopenia virus (FPV), various herpesviruses, non-pathogenic "orphan viruses", enteric viruses such as enterovirus, etc. Other forms of the vaccine are also contemplated. For example, "empty" virion particle vaccines (without nucleic acid) are also contemplated, as are vaccines comprising proteins that are not assembled into a capsid. The RPVs of the invention may also be substantially or partially purified and/or concentrated by panning e.g. with transferrin coated beads in a column, in dishes, etc.

The RPVs of the invention may be safely administered at very high titers. For example, a usual dose of CPV-2 in a vaccine is about 10,000 virus particles per injection. The amount administered when RPV is used ranges from about 10,000 particles per injection to about 100,000 particles per injection, or even higher, e.g. from about 100,000 up to about 1,000,000 particles per injection.

Alternatively, the vaccine preparation may include a VP-2 protein (polypeptide, peptide, etc.) sequence as set forth in SEQ ID NO: 3, or in SEQ ID MO: 4, or antigenic regions or epitopes thereof. Further, sequences which display at least about 50% identity, preferably about 60%, more preferably about 70, 80, or 90% identity or similarity, or even about 95, 96, 97, 98 or 99% or greater identity or similarity to SEQ ID NO: 3 or SEQ ID NO: 4 as described above, or antigenic regions or epitopes thereof are also contemplated for use in the vaccines, so long as the sequence includes one or both of amino acid residues 232 and 300 as Thr and Asp, respectively. The terms "identity" and "similarity" are know in the art, where use of the term "identity" generally refers to a sequence comparison based on identical matches between corresponding identical positions in the sequences being compared.

The term "similarity" refers to a comparison between amino acid sequences, and takes into account not only identical amino acids in corresponding positions, but also functionally similar amino acids in corresponding positions (e.g. Asp and Glu, which both possess a side chain that is usually negatively charged at neutral pH, and thus may function similarly). Thus, similarity between polypeptide sequences indicates functional similarity, in addition to sequence similarity. The sequences encompassed by the invention may differ from those which are explicitly disclosed, for example, by having conservative amino acid substitutions, as are understood by those of skill in the art (e.g. positively charged amino acids may be substituted for one another, negatively charged amino acids may be substituted for one another, aliphatic amino acids may be substituted for one another, etc.), so long as the amino acid sequence retains the ability to elicit an effective, suitable immune response upon administration to a vaccine recipient. Further, the invention also encompasses amino acid sequences of antigenic regions or epitopes that are short contiguous sequences within SEQ ID NO: 3 (i.e. truncated or partial sequences which represent a portion of SEQ ID NO: 3) but which retain the ability to elicit an effective, suitable immune response against the development of symptoms of canine parvovirus infection in a vaccine recipient. Such antigenic regions are generally in the range of about 5-10 amino acids in length, but may be about 15, 20, 25, 30, 35, 40, 45 or even about 50 amino acids or more in length, and will generally encompass one or both of amino acid residues 232 and 300.

In one embodiment of the invention, the vaccine recipient is a puppy. By "puppy" we mean a young dog that is less than about 8 weeks of age. Typically, the vaccine is administered to a puppy at an age of e.g. 2-3 weeks, followed by booster doses at 4 and 6 weeks. In some embodiments, the vaccine is not used after 8 weeks, as after that time, vaccines directed to other known circulating viruses may then be employed without interference by maternal antibodies.

While in some embodiments, the vaccine recipient is a puppy, those of skill in the art will recognize that this need not always be the case. The vaccine may be administered to a dog of any age and to other species of animals (especially carnivores) that are susceptible to infection by parvoviruses, both adults and juvenile animals. Examples include but are not limited to canids (e.g. wild canids such as wolves, wild dog species, coyotes, foxes such as gray, kit and red, etc.], etc.), skunks, cats (including domestic cats and kittens, and larger species of cats, whether domesticated or wild such as bobcats, cougars, lion, tigers, etc.), mink, red panda, etc.; various procyonidae, including raccoons, coatis, kinkajous, olingos, ringtails and cacomistles, etc. Such animals may be domesticated (e.g. pets), "working" animals (e.g. service animals), livestock, animals in the wild, animals in captivity or on reserves, in zoos, in shelters, etc., so long as they can benefit by administration of the vaccine.

The immunogenic/vaccine preparations of the present invention may be administered by any of many suitable means which are well known to those of skill in the art, including but not limited to by injection, administered parenterally, for example, intramuscularly, subcutaneously, intraperitoneally, intradermally or the like, orally via a "puppy lollipop" as described above, intranasally, by ingestion of a food product containing the antigen, etc. However, in preferred a embodiment, the mode of administration to an adult recipient is by injection, and, as described above, the mode of injection to a juvenile is via a solid preparation that dissolves in the mouth upon sucking. The compositions of the invention may be administered alone or in combination with other medicaments or immunogenic compositions, e.g. as part of a multi-component vaccine. Further, administration may be a single event, or multiple booster doses may be administered at various timed intervals to augment the immune response. In the case of administration to puppies, a typical administration regimen would be (as described above) initial administration at e.g. 2-3 weeks of age, followed by booster doses at 4 and 6 weeks. Preferably, administration is prophylactic, i.e. before exposure to the virus has occurred, or is suspected to have occurred, but may also be after the fact, i.e. after a known or suspected exposure, or therapeutically, e.g. after the occurrence of disease symptoms associated with viral infection.

The invention also provides methods of eliciting an immune response in a patient or individual in need thereof, as well as methods of vaccinating a patient or individual (especially a carnivore such as a juvenile canid, e.g. a puppy) against parvovirus infection. The methods include administering one or more doses of an immune eliciting preparation or a vaccine preparation to the recipient. The amount of the dose that is administered is sufficient to elicit an immune response, preferably a protective immune response, to the antigens encoded by the nucleic acids that are administered. Alternatively, in the case of administering one or more amino acid sequences as described herein, the immune response is to the antigens present in the amino acid sequences. Preferably, the immune response is protective and no disease symptoms will occur as a result of administration. However, those of skill in the art will recognize that many effective vaccine compositions cause some relatively minor symptoms upon administration, or attenuate without eliminating all symptoms of disease once the recipient is infected with a disease causing organism. However, the benefits of being protected against full-blown disease far outweigh these possibilities.

In other embodiments, the raccoon parvovirus of the invention is used as a gene delivery system. The raccoon parvovirus (RPV) described herein is an autonomously replicating parvovirus (ARP). The use of ARPs as gene delivery vehicles and expression vectors has been described (see U.S. Pat. No. 5,585,254 to Maxwell, et al.). Since the RPV of the invention is antigenically non-reactive with sera from dogs vaccinated with CPV or which have been naturally exposed to CPV, this RPV is well-suited for use as a gene vehicle and/or expression vector for canines, and also for other species (see below). Genetically engineered RPVs are used to carry into a cell of interest "foreign" or "heterologous" nucleic acid sequences, i.e. sequences which do not originate from RPV, but which encode and express within the cell of interest, or otherwise promote or facilitate expression of, a polypeptide or peptide of interest. For example, one or more immunogens may be encoded and the RPV may be administered to a subject in order to elicit an immune response to the one or more immunogens (e.g. to vaccinate the subject).

RPV is small, non-enveloped single-stand DNA-containing virus. Like other autonomous parvoviruses of vertebrates, the RPV genome has two open reading frames, ORF1 and ORF2 flanked by inverted terminal repeats (ITRs) which are required for DNA replication (FIG. 4A). Expression of ORF1 and OEF2 is driven by promoters P4 and P38, respectively (FIG. 4B). ORF1 encodes non-structural (NS) proteins NS1 and NS2, and ORF2 encodes capsid proteins VP-1, VP-2 and VP-3 (FIG. 4C). NS1 is a multifunctional protein that is necessary for viral DNA replication and promoter trans-activation, such as that which drives transcription of VP-1 and VP-2. NS2 is essential for replication, virus production and nuclear egress of progeny virions. Parvovirus particles have icosahedral symmetry and are about 20 nm in diameter. The particles contain about 50% protein and about 50% DNA, with neutralizing epitopes being present on the exposed surface of the particles.

It is possible to insert heterologous sequences within canine parvovirus capsid proteins, e.g. the VP-2 protein, and the same or similar strategies are used to genetically engineer the RPV of the present invention. (Austin et al., Tropic determinant for canine parvovirus and feline panleukopenia virus functions through the capsid protein VP-2, Journal of General Virology (1997), 78, 925-928.) Table 1 lists restriction sites located within the gene encoding VP-2. One or more of these restriction sites may be used as sites for insertion of foreign DNA.

TABLE 1

Restriction map of VP-2 of Raccoon parvovirus.

| Enzyme | Number of Cuts | [ --------- Base 5' to Cleavage Sites ---------- ] | | | | | | | | |
|---|---|---|---|---|---|---|---|---|---|---|
| AatII | 0 | | | | | | | | | |
| AccI | 3 | 825 | 1048 | 1149 | | | | | | |
| AclI | 0 | | | | | | | | | |
| AcyI | 1 | 1045 | | | | | | | | |
| AflII | 0 | | | | | | | | | |
| AflIII | 0 | | | | | | | | | |
| AgeI | 0 | | | | | | | | | |
| AhaIII | 5 | 159 | 218 | 455 | 1065 | 1611 | | | | |
| AluI | 5 | 64 | 571 | 988 | 1006 | 1615 | | | | |
| AlwNI | 2 | 73 | 472 | | | | | | | |
| ApaBI | 0 | | | | | | | | | |
| ApaI | 0 | | | | | | | | | |
| ApaLI | 1 | 1022 | | | | | | | | |
| ApoI | 9 | 154 | 160 | 437 | 747 | 784 | 879 | 926 | 1409 | 1423 |
| AscI | 0 | | | | | | | | | |
| AsuI | 2 | 1057 | 1360 | | | | | | | |
| AsuII | 0 | | | | | | | | | |
| AvaI | 0 | | | | | | | | | |
| AvaII | 1 | 1360 | | | | | | | | |
| AvrII | 0 | | | | | | | | | |
| BalI | 0 | | | | | | | | | |
| BamHI | 0 | | | | | | | | | |
| BclI | 0 | | | | | | | | | |
| BetI | 0 | | | | | | | | | |
| BglI | 0 | | | | | | | | | |
| BglII | 1 | 577 | | | | | | | | |

TABLE 1-continued

Restriction map of VP-2 of Raccoon parvovirus.

| Enzyme | Number of Cuts | [ --------- Base 5' to Cleavage Sites ---------- ] | | | | | | | | | | |
|---|---|---|---|---|---|---|---|---|---|---|---|---|
| BsaAI | 0 | | | | | | | | | | | |
| BsaBI | 2 | 1109 | 1127 | | | | | | | | | |
| BseMII | 2 | 493 | 1592 | | | | | | | | | |
| BsePI | 0 | | | | | | | | | | | |
| BsiYI | 2 | 34 | 1315 | | | | | | | | | |
| Bsp1407I | 1 | 210 | | | | | | | | | | |
| BspHI | 0 | | | | | | | | | | | |
| BspLU11I | 0 | | | | | | | | | | | |
| BspMII | 0 | | | | | | | | | | | |
| BstEII | 0 | | | | | | | | | | | |
| BstXI | 2 | 380 | 626 | | | | | | | | | |
| Cac8I | 0 | | | | | | | | | | | |
| CauII | 0 | | | | | | | | | | | |
| Cfr10I | 0 | | | | | | | | | | | |
| CfrI | 0 | | | | | | | | | | | |
| ClaI | 0 | | | | | | | | | | | |
| CviJI | 10 | 64 | 295 | 483 | 571 | 863 | 988 | 1006 | 1059 | 1615 | 1627 | |
| CviRI | 12 | 277 | 313 | 346 | 414 | 517 | 532 | 1024 | 1078 | 1141 | 1372 | 1462 |
| | | 1546 | | | | | | | | | | |
| DdeI | 7 | 479 | 581 | 769 | 1007 | 1190 | 1578 | 1621 | | | | |
| DpnI | 6 | 72 | 579 | 716 | 1130 | 1307 | 1538 | | | | | |
| DraII | 0 | | | | | | | | | | | |
| DraIII | 0 | | | | | | | | | | | |
| DrdI | 1 | 1157 | | | | | | | | | | |
| DsaI | 3 | 601 | 625 | 705 | | | | | | | | |
| Eam1105I | 0 | | | | | | | | | | | |
| Eco47III | 0 | | | | | | | | | | | |
| EcoNI | 0 | | | | | | | | | | | |
| EcoRI | 1 | 926 | | | | | | | | | | |
| EcoRII | 2 | 372 | 1488 | | | | | | | | | |
| EcoRV | 1 | 1231 | | | | | | | | | | |
| EspI | 0 | | | | | | | | | | | |
| Fnu4HI | 3 | 569 | 1079 | 1118 | | | | | | | | |
| FnuDII | 0 | | | | | | | | | | | |
| FseI | 0 | | | | | | | | | | | |
| HaeI | 0 | | | | | | | | | | | |
| HaeII | 0 | | | | | | | | | | | |
| HaeIII | 1 | 1059 | | | | | | | | | | |
| HgiAI | 1 | 1026 | | | | | | | | | | |
| HgiCI | 0 | | | | | | | | | | | |
| HgiJII | 0 | | | | | | | | | | | |
| HhaI | 2 | 1098 | 1515 | | | | | | | | | |
| HincII | 2 | 40 | 282 | | | | | | | | | |
| HindIII | 0 | | | | | | | | | | | |
| HinfI | 3 | 469 | 1248 | 1641 | | | | | | | | |
| HpaI | 1 | 282 | | | | | | | | | | |
| HpaII | 0 | | | | | | | | | | | |
| KpnI | 0 | | | | | | | | | | | |
| MaeI | 4 | 680 | 1738 | 1745 | 1799 | | | | | | | |
| MaeII | 1 | 945 | | | | | | | | | | |
| MaeIII | 3 | 321 | 951 | 1569 | | | | | | | | |
| MboI | 6 | 70 | 577 | 714 | 1128 | 1305 | 1536 | | | | | |
| McrI | 0 | | | | | | | | | | | |
| MfeI | 1 | 1310 | | | | | | | | | | |
| MluI | 0 | | | | | | | | | | | |
| MseI | 22 | 158 | 217 | 281 | 368 | 395 | 443 | 454 | 511 | 658 | 1064 | 1259 |
| | | 1265 | 1331 | 1349 | 1366 | 1375 | 1438 | 1522 | 1610 | 1664 | 1682 | |
| | | 1758 | | | | | | | | | | |
| MslI | 2 | 837 | 1457 | | | | | | | | | |
| MstI | 0 | | | | | | | | | | | |
| MwoI | 0 | | | | | | | | | | | |
| NaeI | 0 | | | | | | | | | | | |
| NarI | 0 | | | | | | | | | | | |
| NcoI | 3 | 601 | 625 | 705 | | | | | | | | |
| NdeI | 0 | | | | | | | | | | | |
| NheI | 0 | | | | | | | | | | | |
| NlaIII | 9 | 294 | 313 | 605 | 629 | 709 | 824 | 842 | 1159 | 1456 | | |
| NlaIV | 0 | | | | | | | | | | | |
| NotI | 0 | | | | | | | | | | | |
| NruI | 0 | | | | | | | | | | | |
| NspBII | 1 | 1006 | | | | | | | | | | |
| NspI | 0 | | | | | | | | | | | |
| PacI | 0 | | | | | | | | | | | |
| PflMI | 1 | 34 | | | | | | | | | | |
| PmaCI | 0 | | | | | | | | | | | |

TABLE 1-continued

Restriction map of VP-2 of Raccoon parvovirus.

| Enzyme | Number of Cuts | [ --------- Base 5' to Cleavage Sites ---------- ] | | | | | | | | | | |
|---|---|---|---|---|---|---|---|---|---|---|---|---|
| PmeI | 0 | | | | | | | | | | | |
| PpuMI | 0 | | | | | | | | | | | |
| PshAI | 1 | 35 | | | | | | | | | | |
| PstI | 1 | 279 | | | | | | | | | | |
| PvuI | 0 | | | | | | | | | | | |
| PvuII | 1 | 1006 | | | | | | | | | | |
| RsaI | 6 | 135 | 212 | 711 | 761 | 1385 | 1691 | | | | | |
| RsrII | 0 | | | | | | | | | | | |
| SacI | 0 | | | | | | | | | | | |
| SacII | 0 | | | | | | | | | | | |
| SalI | 0 | | | | | | | | | | | |
| SanDI | 0 | | | | | | | | | | | |
| SauI | 0 | | | | | | | | | | | |
| ScaI | 0 | | | | | | | | | | | |
| ScrFI | 2 | 374 | 1490 | | | | | | | | | |
| SduI | 1 | 1026 | | | | | | | | | | |
| SecI | 4 | 328 | 601 | 625 | 705 | | | | | | | |
| SexAI | 0 | | | | | | | | | | | |
| SfeI | 3 | 65 | 275 | 791 | | | | | | | | |
| SfiI | 0 | | | | | | | | | | | |
| SgfI | 0 | | | | | | | | | | | |
| SgrAI | 0 | | | | | | | | | | | |
| SmaI | 0 | | | | | | | | | | | |
| SmlI | 1 | 198 | | | | | | | | | | |
| SnaBI | 0 | | | | | | | | | | | |
| SpeI | 1 | 679 | | | | | | | | | | |
| SphI | 0 | | | | | | | | | | | |
| SplI | 0 | | | | | | | | | | | |
| SrfI | 0 | | | | | | | | | | | |
| Sse8387I | 0 | | | | | | | | | | | |
| Sse8647I | 0 | | | | | | | | | | | |
| SspI | 2 | 1257 | 1701 | | | | | | | | | |
| StuI | 0 | | | | | | | | | | | |
| StyI | 4 | 328 | 601 | 625 | 705 | | | | | | | |
| SwaI | 2 | 159 | 218 | | | | | | | | | |
| TaqI | 0 | | | | | | | | | | | |
| TatI | 2 | 210 | 759 | | | | | | | | | |
| TfiI | 3 | 469 | 1248 | 1641 | | | | | | | | |
| TseI | 3 | 568 | 1078 | 1117 | | | | | | | | |
| sp45I | 0 | | | | | | | | | | | |
| Tsp4CI | 2 | 34 | 462 | | | | | | | | | |
| TspEI | 25 | 154 | 160 | 237 | 261 | 317 | 389 | 437 | 730 | 747 | 784 | 879 |
| | | 926 | 1310 | 1328 | 1409 | 1423 | 1482 | 1495 | 1518 | 1565 | 1600 | |
| | | 1646 | 1678 | 1715 | 1750 | | | | | | | |
| TspRI | 0 | | | | | | | | | | | |
| Tth111I | 0 | | | | | | | | | | | |
| VspI | 2 | 658 | 1664 | | | | | | | | | |
| XbaI | 0 | | | | | | | | | | | |
| XcmI | 1 | 1241 | | | | | | | | | | |
| XhoI | 0 | | | | | | | | | | | |
| XhoII | 4 | 70 | 577 | 714 | 1305 | | | | | | | |
| XmaIII | 0 | | | | | | | | | | | |
| XmnI | 0 | | | | | | | | | | | |

Restriction sites that will be particularly useful for inserting nuclei acid sequences into the VP-2 gene include EcoRI, HpaI, and PstI. This is because these restriction sites are commonly engineered in the multiple cloning sites of most recombinant vectors.

Autonomous parvoviruses are generally limited to packaging a total of amount of DNA equal to about 105% of their wild DNA content. Thus, preferred transgenes or portions thereof (i.e. heterologous or foreign nucleotide sequences, nucleic acid sequences which do not naturally occur in parvoviruses, etc.) for inclusion in the RPV gene delivery vehicles of the invention are generally from about 9 to about 60 nucleotides in length. For example, sequences of about 60 nucleotides or less (e.g. about 10, 15, 20, 25, 30, 35, 40, 45, 50 or 55 nucleotides) can be readily accommodated. Such sequences generally encode sequences of interest (e.g. small proteins, polypeptides, peptides, etc.) comprising from about 3 to about 20 amino acids e.g. about 3, 4, 5, 6, 7, 8, 9, 19, 11, 12, 13, 14, 15, 16, 17, 18, 19, or 20 amino acids. In one embodiment, peptides up to 12 amino acids encoded by 36 nucleotides are accommodated by the RPV. However, in other embodiments, significantly more nucleic acid sequences are inserted by replacing portions of the VP-2 protein by the foreign DNA. For example, in some embodiments, from about 50 to 550 amino acids are replaced, e.g. about 50, 100, 150, 200, 250, 300, 350, 400, 450, 500, or even 550 (the entire VP-2 gene) are replaced by foreign DNA, with retention or addition of the required inverted repeats.

Sequences of interest encoded by the heterologous nucleotide sequences may include, for example, one or more epitopes or antigenic regions of interest from a protein of interest, examples of which include but are not limited to:

surface proteins of important pathogens of dogs, cats and other species; cassettes of linear epitopes of canine distemper virus, canine adenovirus and/or canine influenza virus surface protein; multiple peptides selected from hemagglutinin of canine distemper virus and canine influenza virus; the aminogenic epitope of canine parvovirus; the amino epitope of canine adenovirus (derived from the penton protein), etc. Additional epitopes of some important canine viruses have been defined. (See, for example, Sugai et al, *Microbiol Immunol.* 53(12):667-74, 2009; Jung et al, *J Vet Sci.* 6(1):21-4, 2005; Ghosh et al, *Immunology* 104(1):58-66, 2001; etc.).

In other embodiments, the encoded polypeptide/peptide has a function or properties other than (or in addition to) that of eliciting an immune response, e.g. cytotoxicity to tumor cells, targeting properties, etc.

Figure 5A:
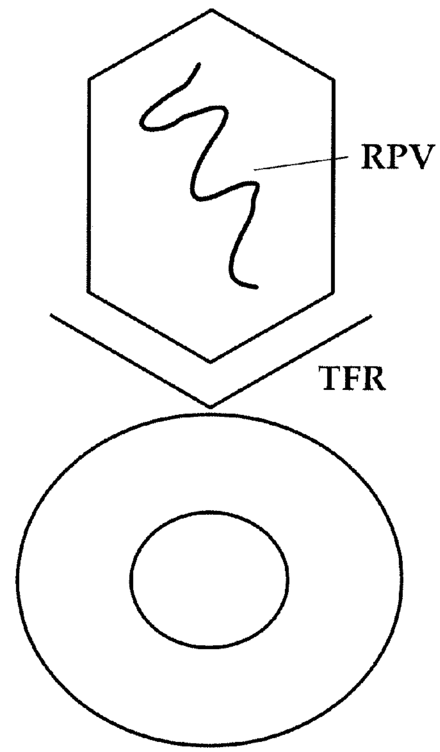
FIGS. 5A and B. A, Schematic of raccoon parvovirus binding to cell surface transferrin receptor (TFR); B, schematic of general strategy for preparing autonomous parvovirus vectors.

In some embodiments of the invention, the RVP gene delivery vehicle may be further genetically engineered to permit targeting of the RVP to a cell type or cell types of interest. Like other carnivore parvoviruses (and also rodent arena viruses), raccoon parvoviruses enter cells by binding to cell surface transferrin receptors (TFR), as illustrated schematically in FIG. 5A. By manipulating and mutating the cognate transferrin binding sites of RPV (anti-receptor sites), (e.g. proteins VP-1, VP-2 and/or VP-3), it is possible to alter the host range of the virus and/or the cell type which the RPV can infect. For example, such genetically engineered RPV are able to bind to transferrin receptors and infect cells of species other than raccoon (including humans), and can thus be used as gene delivery vehicles in species other than canines. Alternatively, RPVs with altered host ranges can be identified and selected during passage of the virus in cells from a variety of species. There are generally two ways to achieve targeting specificity, transductional targeting and transcriptional targeting. Transductional targeting involves the selective uptake of the vector into the cells of interest, for example, dividing cells of canine cancers, intestinal cells, etc. This may occur by genetically modifying the virus to contain and express factors necessary for binding to and infecting a cell of interest, e.g. ligands (e.g. cognate ligands, which may be proteins) which bind receptors located exclusively (or almost exclusively) on the surface of the cell of interest, and which cause or permit uptake of the virus by the cell of interest. For example, transductional targeting with an RPV is generally carried out by genetically engineering the RPV to express on its outer surface a cognate ligand of a receptor type that is found only on the targeted cell. In transcriptional targeting, although the transgene may be taken by many different host cells it is transcribed only in target cells. Transcriptional targeting with an RPV is generally carried out by including a cell specific and/or inducible promoter in the construct to drive expression of the heterologous sequences of interest only (or almost exclusively) in the targeted cells.

Figure 5B:
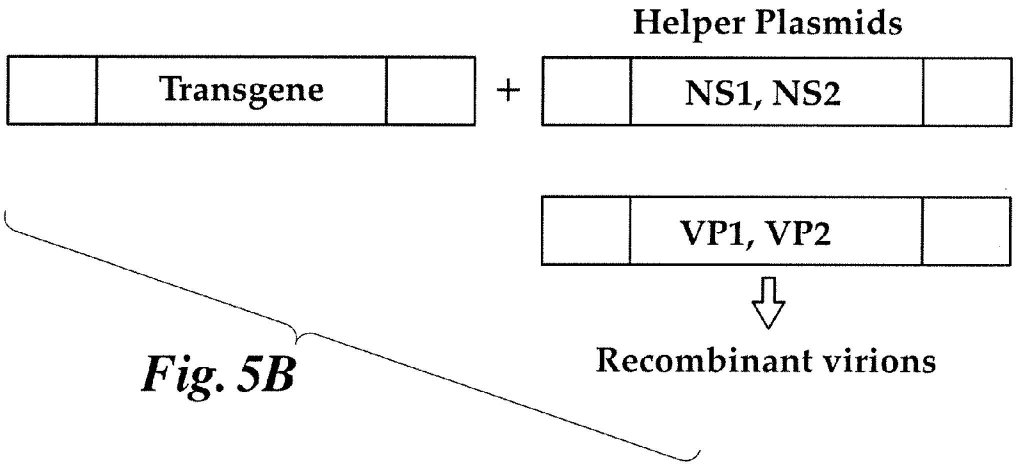

A general strategy for preparing autonomous parvovirus vectors has been described by Maxwell et al., (Methods 28 (2002) 168-181), and RPV viral vector production can be adapted as described therein, e.g. similarly to production of the LuIII vector. Briefly, a productive cell line such as CRFK is used. Producer cells (such as the 324K cell line) are transfected with supercoiled forms of a recombinant RPV plasmid containing transgene sequences of interest, together with one or more plasmids expressing the required helper functions for excision, amplification and packaging of the virus particles e.g. NS1, NS2, VP1, VP-2, etc. This process is illustrated schematically in FIG. 5B. Strategies for making recombinant plasmids for canine and feline parvoviruses have been described (Austin et al., *Journal of General Virology* (1996), 77, 1787-1792) and the same or similar strategies are used to make recombinant RPV plasmids. The RPV vectors are harvested from cell extracts prepared several days after transfection.

Virotherapy for tumors is now being explored (see, for example, Rommelaere et al, *Cytokine* & *Growth Factor Reviews* 21:185-195, 2010; and U.S. Pat. No. 7,179,456 to Rommelaere et al, the complete contents of which are herein incorporated by reference). However, there is a need for novel viruses that can carry out the targeted attacks. The RPV of the invention can be used in this manner, i.e. as tumor therapy agent. The use of the RVP in this manner generally involves the identification of a subject with a tumor in which the RVP is able to replicate, and administration of the RVP to the subject that bears the tumor. Administration may be carried out in any suitable manner, including but not limited to intravenously, by injection directly into the tumor (i.e. intratumoral administration), etc. RPV virotherapy is mainly intended for a single-administration (e.g. "one-shot") treatment. This is because once the subject (e.g. a dog) receives the RPV, it will respond immunologically by creating antibodies to the RPV. Thus, the possibility of giving an effective second shot is less likely. Thus, the one dose that is administered has a very high parvovirus concentration. For example, the dose will range from at least about 10 million to 100 million virus particles per dose per dose. Only RPV can be administered in an adult dog to cause no diarrhea and kill residual tumor cells in a diffuse tumor. Only RPV (but not, for example, CPV-2 or FPLV) can be used at these very high doses and yet cause no clinical disease in the recipient, i.e. RPV will not cause diarrhea in a tumor bearing dog or cat.

Subjects with tumors which may be treated in this manner include but are not limited to, for example, dogs, cats, pet minks, raccoons and humans, the therapy being highly efficacious for dogs and cats. The subject may be a juvenile or an adult. Types of tumors which may be treated with the RPV of the invention include but are not limited to: for dogs, histiocytic sarcoma (which are diffuse and for which no successful treatment is currently available), pancreatic cancers, lymphomas, gliomas, and osteosarcoma, etc.; for cats, the tumors listed above and also hepatobiliary tumors, etc.

In one embodiment, the RPV that is used to treat the tumor is genetically engineered to specifically target the tumor cells so that viral binding to the tumor cells is selective or, preferably, specific. This use of the RVP of the invention may also be carried out, for example, in adult dogs, since even if they have been previously vaccinated against CPV, the antibodies they carry will not fully neutralize the RPV of the invention.

The invention also provides diagnostic kits for the detection of the raccoon parvoviruses described herein. Such kits may include oligonucleotide primers specific for amplifying (e.g. by polymerase chain reaction) the nucleic acid sequences disclosed herein. Alternatively, such kits may include antibodies (e.g. monoclonal or polyclonal) that bind selectively or specifically to unique antigenic determinants displayed by the parvoviruses, e.g. for Asp at position 300 of the VP-2 protein. Methods of detecting the RPVs are also encompassed. Such methods generally involve obtaining a biological sample from a subject suspected of being infected with an RPV of the invention, and detecting the presence or absence of an RPV of the invention in the sample, e.g. using oligonucleotide primers specific for amplifying (e.g. by polymerase chain reaction) the nucleic acid sequences disclosed herein, and/or by using antibodies specific for the RPVs disclosed herein. Methods of diagnosing infection of an animal with the RPVs (e.g. MoAb that react with RPV and raccoon kidney cell culture) using these methods are also provided.

The foregoing examples serve to illustrate the invention but should not be construed as limiting in any way.

EXAMPLES

Example 1

Isolation of a Novel Parvovirus from a Raccoon

The common North American raccoon (*Procyon lotor*) is a nocturnal omnivore that has adapted well to urban habitats. Raccoons prefer to live near river banks that provide shelter and food; in urban setting they may interact with dogs and cats. Raccoons are susceptible to some diseases that affect carnivores, especially canine distemper, rabies, canine adenovirus, leptospirosis, influenza A and parvovirus. There are previous reports of the detection and characterization of parvovirus from raccoons in Canada (Barker et al., 1983) and the USA (Nettles et al., 1980); however, there are no published reports in the past two decades. It has also been reported that raccoons are not susceptible to canine parvovirus type 2 (CPV-2) (Appel and Parrish, 1982). However, as disclosed herein evidence is provided that suggests that this is not the case. Moreover, the present disclosure describes the isolation of a parvovirus genetically related to CPV-2 in a rescued raccoon at a wildlife rehabilitation facility in the USA.

A two-month-old male raccoon was admitted to wildlife rehabilitation in Arkansas, USA. The raccoon was clinically normal at the time of admission. After 4 weeks, the raccoon developed loss of appetite and severe diarrhea. The raccoon was treated with enrofloxacin (Baytril, Bayer) administered once a day, and fluids were administered subcutaneous. Despite this treatment, the animal died. Two other raccoons had previously died in the same facility one after showing similar clinical signs. The raccoon was submitted to the Oklahoma Animal Disease Laboratory for postmortem examination.

On gross examination, the oral mucosa and sclera were pale to white, the abdomen was distended and the perineum and anal areas were covered with thin 'runny' yellow fluid. The animal weighed 1.5 kg and had adequate skeletal muscle and body fat stores, consistent with acute death. The stomach contents were mucoid yellow with yellow granular material. The small intestine was dilated and red, with rough serosa. The contents of both the small and large intestines were runny, mucoid and yellowish, with yellow material coating a smooth glassy mucosa.

Histopathological examination revealed that the spleen was congested and the follicles were depleted of lymphocytes with lymphoid necrosis. Diffuse pulmonary edema was evident in the lungs. Sections of small intestine had widespread crypt necrosis with sloughing of the villi and collapse of the remaining lamina propria. A few areas revealed scattered, large, hyperchromatic regenerating crypt epithelial cells. The intestinal luminal surface was coated with fibrin, neutrophils, bacteria and some hemorrhage. Immunohistochemistry for CPV revealed rare positive signals, which were evaluated as equivocal. The microscopic appearance of the intestine was consistent with viral enteritis.

Fresh sections of the intestine and tongue were examined by the fluorescent antibody test with monoclonal antibody 3B10 (fluorescein isothiocynate-labeled anti-CPV conjugate; MVRD) (Kapil et al., 2007). Both tissues were found to be negative. Based on the histopathological findings, there were few enterocytes remaining in the intestine that could have contained virus. The general PCR for carnivore parvovirus, as developed by Desario et al., (2005), was carried out twice on the intestinal contents, and was strongly positive both times. To further support the virology findings, the intestinal contents were inoculated onto cultured Crandall-Reese feline kidney (CRFK) cells (ATCC).

For virus isolation, the sample of intestine was prepared as a 10 percent w/v suspension and freeze-thawed once. The suspension was extracted with an equal volume of chloroform. After centrifugation at 10,000 g for five minutes, the supernatant was filtered through a 0.22 μm syringe filter. The filtrate was inoculated onto CRFK cells approximately 45 minutes after plating in the flasks. The cells were observed daily for 5 days, and on the fifth day cytopathology characterized by rounding and detachment of cells was observed. The cells were freeze-thawed twice and subjected to a hemagglutination test with porcine erythrocytes. The sample showed hemagglutinating activity, that parvovirus had replicated in the cell culture. The presence of the virus was further confirmed by the general parvovirus PCR (Desario et al., 2005) on the cell culture supernatant, followed by sequencing of the amplicon.

Three independent sequences were obtained from the same specimen (AR-08071304). All the sequences were the same. Two were derived from the fresh sample of intestinal contents, and the third was derived from the isolate cultured in CRFK cells. The three sequences were subjected to BLASTN analysis and CLUSTALW analyses (National Center for Biotechnology Information). Based on sequence analysis, the raccoon parvovirus was found to be genetically most closely related to CP-V2.

Figure 6:
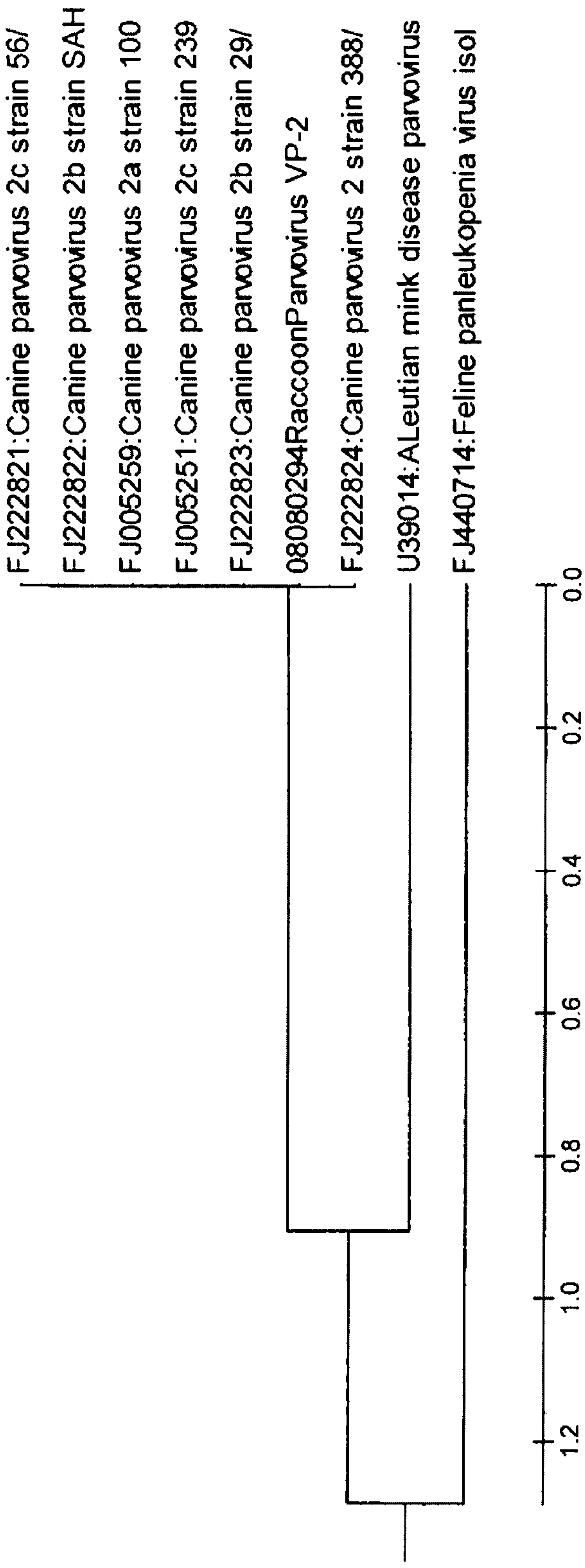
FIG. 6. Relatedness of the newly isolated raccoon parvovirus to other similar viruses.

To completely sequence the viral protein-2 (VP-2) of the raccoon parvovirus, two additional PCR amplifications were performed as described by Decaro et al., (2008). The complete VP-2 sequence of the raccoon parvovirus was subjected to BLAST analysis. The sequence had highest identity with CPV (98 percent); and had an identity of 97 percent with isolates of feline panleukopaenia virus, another raccoon parvovirus (M24005), and mink enteritis virus (FIG. 6).

In experimental studies, raccoons have been found to be susceptible to mink enteritis virus and feline parvovirus (Barker et al., 1983). The raccoon isolate described here had biological and sequence homology with CPV-2. Approximately 500 base pairs of the partial sequence of VP-2 had highest homology (99 percent) with CPV-2. The codons at positions 426 and 555 helped classification of the raccoon isolate as CPV-2 (Desario et al., 2005). Moreover, codons 564 and 568 were also consistent with CPV-2 (Truyen et al., 1994). Codon 564 in the raccoon isolate was AGT, as it is in canine parvovirus; this codon 564 is AAT in feline parvovirus and the previous raccoon isolate (M24005). Codon 568 is GGT in both CPV-2 and the present raccoon isolate; however, it is GCT in feline parvovirus and the previous raccoon isolate (M24005).

Similarly, based on the amino acid sequence of VP-2, the raccoon parvovirus may be considered to be a unique variant of CPV-2. At amino acid position 80 of VP-2, the raccoon isolate had arginine, the same as VP-2 from CPV isolates; in contrast, feline parvovirus has lysine at amino acid position 80. At amino acid position 87, the raccoon isolate had a leucine residue, like the variants of CPV-2, CPV-2a and CPV-2b; both FPV and CPV-2 have methionine at amino acid position 87. At amino acid position 93, the raccoon isolate had asparagine, like all CPVs, while FPV has lysine at this amino acid position. At amino acid position 101, the raccoon isolate had threonine, similar to CPV-2a and CPV-2b; both FPV and CPV-2 had isoleucine at amino acid position 101. At amino acid position 103, the raccoon parvovirus had alanine, like CPV-2a and CPV-2b, whereas FPV and CPV-2 have valine at amino acid position 103. The raccoon parvovirus had threonine at amino acid position 232, serine at amino acid position 297 and aspartic acid at amino acid position 300; FPV and CPV-2 have alanine at amino acid position 300, while CPV-2a and CPV-2b have glycine at amino acid position 300. At amino acid position 305, the raccoon isolate had aspartic acid, like FPV and CPV-2; CPV-2a and CPV-2b have tyrosine at this amino acid position. The raccoon parvovirus had asparagine at amino acid position 426, like FPV, CPV-2, and CPV-2a. At amino acid position 555, the raccoon isolate had valine, like most CPV genotypes and FPV; however, CPV-2a has isoleucine at amino acid position 555. At amino acid position 564, the raccoon isolate had serine, like all CPV isolates; FPV has asparagine at this amino acid position. At amino acid position 568, the raccoon parvovirus had glycine, like CPV-2; FPV has alanine at this amino acid position. Thus, based on the complete VP-2 sequence of the raccoon parvovirus isolate (CAR-08071304), it was considered to be a unique genetic variant of CPV-2. A summary of these differences is shown in FIG. 7.

Notably, amino acid residue 232 is Thr in the raccoon isolate and amino acid residue 300 is Asp. These two amino acid residues in the VP-2 protein of RPV are thus distinct from the VP-2 proteins of all other known CPV isolates and may be responsible for the unique properties (e.g. antibody reactivity) of this RPV. In particular, substitution of amino acid residue 300 from Gly (uncharged, side chain ═H) to Asp (negative charge at neutral pH, side chain=$CH_2COO^-$) alters the antigenic properties of the virus. Without being bound by theory, it is likely that this change also affects the receptor binding properties of the virus.

The previous raccoon isolate M24005 was isolated in the USA in 1979. The present isolate was antigenically different from current circulating CPV-2 isolates in USA, based on its lack of reactivity with the monoclonal antibody A3B10 (Kapil et al., 2007). Virus isolation-positive tissue was negative by direct fluorescent antibody testing. On the basis of the histological findings, few enterocytes were present lining the intestines when the raccoon died. The lack of reactivity with A3B10 was not surprising, because this monoclonal antibody reacts with a major antigenic domain of CPV-2 (Wikoff et al., 1994). The intestinal contents were negative for parasitic ova by direct examination and fecal floatation test. The intestinal contents were negative for parasitic ova by direct examination and the faecal flotation test, and negative on ELISA for *Clostridium difficile* toxin. *Streptococcus dysgalatiae* subspecies *equisimilis* and *Streptococcus uberis* were isolated from a sample of lymph node by routine bacteriological examination. Secondary bacterial contaminants or their toxins may have contributed to the death of the raccoon.

Due to the likely interactions of raccoons with companion animals in urban areas of the USA, this finding is epidemiologically significant. Based on a published survey from Canada (Barker et al., 1983), raccoons may be frequently exposed to CPV-2. In the study of Barker et al., (1983), 25 of out of 112 raccoons (22.4 percent) tested in Canada were seropositive; with most animals positive at hemagglutination-inhibition titres equal to or greater than 1:256. Raccoons have also been implicated in the spillover of FPV to zoo animals in urban environments (Junge et al., 2007). Raccoons may be exposed to CPV-2 due to their omnivorous nature and feeding habits. The role of urban raccoons in the transmission of CPV-2 to other species requires further investigation. There is no published evidence of natural CPV-2 infection in raccoons. However, based on a hemagglutination assay, CPV-2 was implicated in a captive raccoon in the USA based upon hemagglutination of porcine erythrocytes at pH 7.2 (Nettles et al., 1980); the genome sequence was not determined in that study.

Example 2

Reactivity of Carnivore Parvoviruses with Commercially Available Monoclonal Antibodies Testing of the new isolate was carried out using four additional commercially available antibodies, CPV1-24, CPV1-13 and CPV1-5 (Custom Monoclonal Antibodies, Sacramento, Calif.). These canine parvovirus-2 antibodies are commercially available for routine diagnosis of canine parvovirus-2. The results are presented in Table 2. As can be seen, the antibodies react similarly with CPV, FPLV and RPV. This shows that some immunogenic epitopes are conserved among these viruses.

TABLE 2

Antibody testing of three additional raccoon isolates

| Isolate description | | | CPV Monoclonal Antibodies | | | |
|---|---|---|---|---|---|---|
| 440 Codon | | Assigned # | CPV1-2 | CPV1-24 | CPV1-13 | CPV1-5 |
| GCA | CPV-2c | 08060974 | − | − | ± | + |
| GCA | CPV-2c | 08090386 | − | − | ± | + |
| ACA | CPV-2c | 07030244 | − | − | ± | + |
| ACA | CPV-2c | 07080797 | − | − | ± | + |
| ACA | CPV-2c | 07051347 | − | − | + | + |
| | CPV-2b | 08070185 | − | − | ± | + |
| | CPV-2b | 07030847 | − | − | ± | + |
| | FPV | 08120386 | − | − | ± | ± |
| | FPV | 08061339 | − | − | − | − |
| | RPV, pH 7.2 | 08071304 | − | − | ± | + |
| | RPV, pH 6.5 | 08071304 | − | − | ± | + |

Example 3

Reactivity of Three Other Raccoon Parvoviruses with a Panel of Monoclonal Antibodies In addition to the Arkansas raccoon parvovirus 08071304 described above, three additional parvoviruses of raccoon origin but from Illinois were tested with respect to reactivity with the 3B10 MoAb (VMRD, WA) using fluorescent antibody testing. 3B10 MoAb is specific for CPV-2 and is frequently used to identify and/or diagnose parvovirus infection in dogs. All three viruses tested negative with 3B10 MoAb. Thus, as was the case for the RPV described in Examples 1 and 2, no epitopes of these three additional raccoon viruses were recognized by this CPV-2 MoAb antibody.

These results demonstrate that these three parvoviruses, like RPV, also have a mutation at amino acid position 300 of VP-2, since these intestinal tissue samples did not react with the 3B10 MoAb, which is known to react with an epitope that includes the amino acid at position 300 in other parvoviruses.

Example 4

Sequencing of Gene Encoding The VP-2 Proteins of the Three Additional Raccoon Parvoviruses The gene encoding the VP-2 protein of each of the three viruses described in Example 3 was partially sequenced and the results are presented below.

Inverse-Complement for 10071191-A, nucleotide positions 1216 to 1773 (i.e. 557 nucleotides in length):

```
                                        (SEQ ID NO: 5)
TCAGGAAGATATCCAGAAGGAGATTGGATTCAAAATATTAACTTTAA

CCTTCCTGTAACAAATGATAATGTATTGCTACCAACAGATCCAATTG

GAGGTAAAACAGGAATTAACTATACTAATATATTTAATACTTATGGT

CCTTTAACTGCATTAAATAATGTACCACCAGTTTATCCAAATGGTCA

AATTTGGGATAAAGAATTTGATACTGACTTAAAACCAAGACTTCATG

TAAATGCACCATTTGTTTGTCAAAATAATTGTCCTGGTCAATTATTT

GTAAAAGTTGCGCCTAATTTAACAAATGAATATGATCCTGATGCATC

TGCTAATATGTCAAGAATTGTAACTTACTCAGATTTTTGGTGGAAAG

GTAAATTAGTATTTAAAGCTAAACTAAGAGCCTCTCATACTTGGAAT

CCAATTCAACAAATGAGTATTAATGTAGATAACCAATTTAACTATGT

ACCAAGTAATATTGGAGGTATGAAAATTGTATAGAAAAATCTCAACT

AGCACCTAGAAAATTATATTAACAACTTAGCTAGTCTTAT
```

Inverse-Complement for 10071191-B, nucleotide positions 1214 to 1779 (565 nucleotides in length):

```
                                        (SEQ ID NO: 6)
GGTCAGGAAGATATCCAGAAGGAGATTGGATTCAAAATATTAACTTTA

GCCTTCCGGTGGCAAATGATAATGTATTGCTGCCAACAGGTCCAATTG

GAGGTAAAACAGGAATTAACTATACTAATATATTTAATACGTATGGTC

CTTTAACTGCATTAAATAATGTACCACCAGTTTATCCAAATGGTCAAA

TTTGGGATAAAGAATTTGATACTGACTTAAAACCAAGACTTCATGTAA

ATGCACCATTTGTTTGTCAAAATAATTGTCCTGGTCAATTATTTGTAA

AAGTTGCGCCTAATTTAACAAATGAATATGATCCTGATGCATCTGCTA

ATATGTCAAGAATTGTAACTTACTCAGATTTTTGGTGGAAAGGTAAAT

TAGTATTTAAAGCTAAACTAAGAGCCTCTCATACTTGGAATCCAATTC

AACAAATGAGTATTAATGTAGATAACCAATTTAACTATGTACCAAGTA

ATATTGGAGGTATGAAAATTGTATAGAAAAATTCTCAAACTAGCACCT

AGAAAATTATATAACAACTTTACTTCTGGTGGGCGGG
```

Inverse-Complement for 10071191-C, nucleotide positions 1216 to 1774 (556 nucleotides in length):

```
                                        (SEQ ID NO: 7)
TCAGGAAGATATCCAGAAGGAGATTGGATTCAAAATATTAACTTTAAC

CTTCCTGTAACAAATGATAATGTATTGCTACCAACAGATCCAATTGGA

GGTAAAACAGGAATTAACTATACTAATATATTTAATACTTATGGTCCT

TTAACTGCATTAAATAATGTACCACCAGTTTATCCAAATGGTCAAATT

TGGGATAAAGAATTTGATACTGACTTAAAACCAAGACTTCATGTAAAT

GCACCATTTGTTTGTCAAAATAATTGTCCTGGTCAATTATTTGTAAAA

GTTGCGCCTAATTTAACAAATGAATATGATCCTGATGCATCTGCTAAT

ATGTCAAGAATTGTAACTTACTCAGATTTTTGGTGGAAAGGTAAATTA

GTATTTAAAGCTAAACTAAGAGCCTCTCATACTTGGAATCCAATTCAA

CAAATGAGTATTAATGTAGATAACCAATTTAACTATGTACCAAGTAAT

ATTGGAGGTAGAAAATTGTATAGAAAAATCTCAACTAGCACCTAGAAA

ATTATATTAACAACTTAGCTAGGCGTAT
```

These are partial VP-2 sequences of RPV from Chicago, Ill. Thus, amino acid residue 300 was not sequenced. However, the lack of reactivity with 3B10 MoAb (see Example 3) indirectly supports that the mutation at amino acid position 300 is also present in these viruses. Alignment of the four sequences (namely the full length 08071304 with the three partial sequences 10071191-1,2,3) and revealed some differences. The first significant change is that at nucleotide 1216, of 08071304 has an "A", whereas all three newly identified RPVs (10071191A, B and C) have a "T". All four sequences are identical from nucleotides 1217 to 1261. However, at nucleotide position 1262 of 10071191-B, there is a "G" instead of an "A" which is present in the other 3 sequences. From nucleotides 1263 through 1268, all the sequences are identical. However, at nucleotide position 1269, sequence 10071191-B has a "G" instead of a "T" which is present in the other three sequences. Similarly, at nucleotide positions 1272 and 1273, 10071191-B has "GG" instead of "AA" which is present in the other three sequences. From nucleotides 1274 through 1292 all four sequences are identical. However, at nucleotide position 1293 all sequences have an "A" but 10071191-B has a "G". From nucleotide 1294 through 1300 all sequences are identical, but then at nucleotide position 1301, 10071191-B has a "G" rather than an "A". From nucleotide 1302 through 1349 all sequences are identical, but at nucleotide position 1350 all sequences have a "T" but 10071191-2 has a "G". From nucleotide position 1351 all sequences are identical up to nucleotide position 1706.

Based on this we conclude that one isolate, 10071191-B, has a base point mutation to "G" in several locations of the VP-2 gene.

Experiments conducted with respect to culturing these 3 new RPVs showed that 10071199-A can be propagated in cell culture, and that 10071199-C is highly cytopathic in the CRFK cell line.

Example 5

Phylogenetic Comparison of the New Raccoon Parvovirus Isolates 0808294, 10071191-1, 10071191-2 and 10071191-3 with Other Known Carnivore Parvoviruses To construct a more extensive phylogenetic tree of carnivore parvoviruses, the full length sequence encoding the VP-2 protein of new raccoon parvovirus isolate 0808294, the partial sequences encoding the VP-2 protein of raccoon isolates 10071191-1, 10071191-2 and 10071191-3 VP-2, and several other CPV-2 parvovirus sequences (available from the National Center for Biotechnology Information (NCBI) website) were compared. All sequences were first converted to FASTA formats and then aligned using the CLUSTAL/W program of the MEGA 4.1 software. The tree was constructed using Bootstrap analysis and the hierarchical clustering method UPGMA (Unweighted Pair Group Method with Arithmetic Mean).

Figure 8:
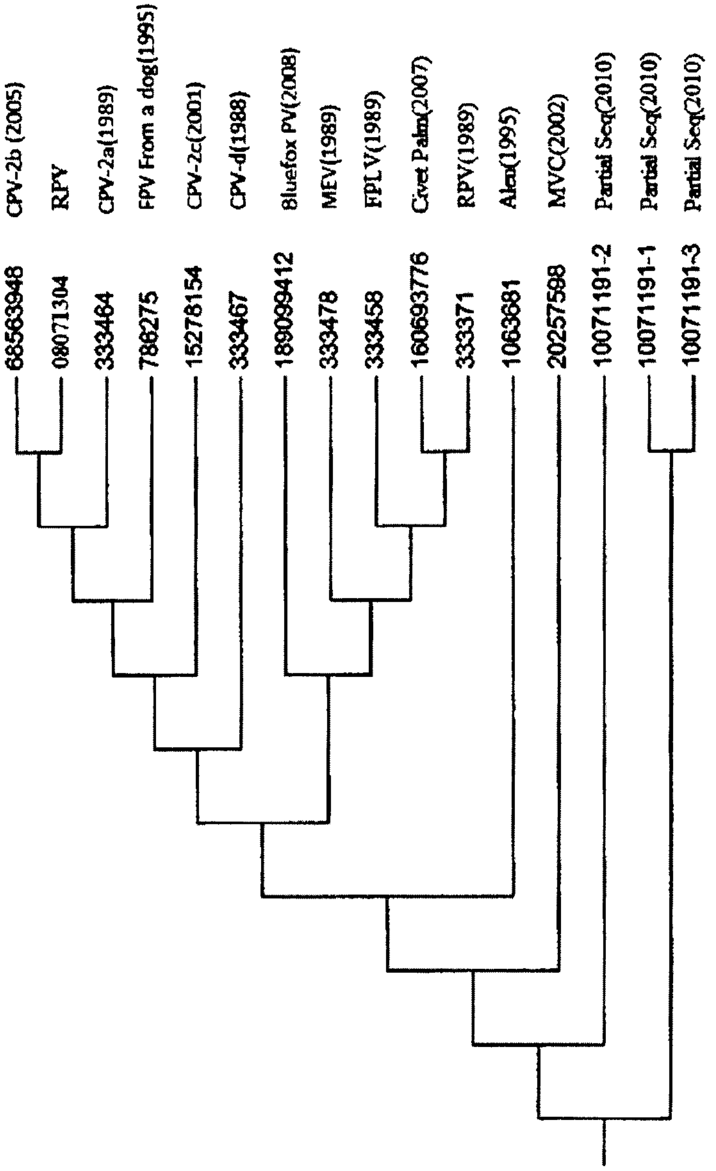
FIG. 8. Phylogenetic tree comparing the VP-2 protein of the newly isolated raccoon parvovirus with those of other carnivore parvoviruses. CPV=canine parvovirus; RPV=raccoon parvovirus; FPV=feline parvovirus; PV=parvovirus; MEV=mink enteritis virus; FPL=feline panleukopenia virus; Aleu=Aleutian mink disease parvovirus; MVC=minute virus of canines.

The results are depicted in FIG. 8, which shows the NCBI GI numbers of each isolate. As can be seen, the Arkansas RPV (08071304) clusters with the well characterized canine parvoviruses. Thus, evolutionarily it is a canine parvovirus-2 like virus.

Example 6

Basic Local Alignment Search Tool (BLAST) Analysis of Full Length 08071304 RPV VP-2 Sequence The 1801 nucleotide sequence of 08071304 RPV VP-2 was analyzed using BLAST analysis. The results showed that this sequence exhibits high homology with other carnivore parvoviruses.

The first 7 highest identities (99%) were with canine parvoviruses. Surprisingly several 98% identities were obtained with feline panluekopaenia. There was 98% identity score with a raccoon parvovirus (M24005.1) and there was also 98% identity with mink enteritis virus. This is unusual for parvovirus VP-2 sequences, in that such high levels of identity are not usually observed amongst several different carnivore parvoviruses. Normally, a canine parvovirus aligns and shows high identity only with other canine parvoviruses, feline panleukopaenia shows the highest identity with other feline panleukopaenia viruses, etc. It thus appears that 08071304 is a chimeric carnivore parvovirus. This observation is further supported by the amino acid comparisons shown in FIG. 7. In the past, carnivore parvoviruses were easy to classify based on the amino acid sequence of VP-2. Interestingly, the RPV (08071304) of the invention does not follow the linear VP-2 DNA convention and rules. At some places, as shown in FIG. 7, the amino acid that is at a critical epitope is like that of FPV or MEV (e.g. at amino acid position 305). However, at amino acid position 93, it is like CPV. Thus, 08071307 RPV is unique genetically, antigenically and with respect to amino acid sequence. This virus would likely provide a common carnivore parvovirus for overcoming maternal derived immunity in several species.

REFERENCES

APPEL, M. J. & C. R. PARRISH. (1982). Raccoons are not susceptible to canine parvovirus. Journal of American Veterinary Medical Association 18, 489.

AUSTIN et al. (1997). Tropic determinant for canine parvovirus and feline panleukopenia virus functions through the capsid protein VP-2, Journal of General Virology 78, 925-928.

BARKER, I. K., POVEY, R. C., & D. R. Vogt. (1983). Response of mink, skunk, red fox, and raccoon to inoculation with mink virus enteritis, feline panleukopenia and canine parvovirus and prevalence of antibody to parvovirus in wild carnivores in Ontario. Canadian Journal of Comparative Medicine 47, 188-197.

DECARO, N., DESARIO, C., MICCOLUPO, A., CAMPOLO, M., PARISI, A., MARTELLA, V., AMOR ISCO, F., LUCENTE, M. S., LAVAZZA, A., AND BUONAVOGLIA, C. 2008. Genetic analysis of feline panleukopaenia viruses from cats with gasteroenteritis. Journal of General Virology 89, 2290-2298.

DESARIO, C., DECARO, N., CAMPOLO, M., CAVALLI, A., CIRONE, F., ELIA, G, MARTELLA, V., LORUSSO, E., CAMERO, M., & BUONAVOGLIA, C. 2005. Canine parvovirus infection: which diagnostic test for virus? Journal of Virological Methods 126, 179-185.

GHOSH et al., (2001). Identification of canine helper T-cell epitopes from the fusion protein of canine distemper virus, Immunology 104(1):58-66.

JUNG et al, (2005). Induction of castration by immunization of male dogs with recombinant gonadotropin-releasing hormone (GnRH)-Canine distemper virus (CDV) T helper cell epitope p35, J Vet Sci. 6(1):21-4

JUNGE, R. E., BAUMAN, K., KING, M., & GOMPPER, M. E. (2007). Serologic assessment of exposure to viral pathogens and *Leptospira* in an urban raccoon (*Procyon lotor*) population inhabiting a large zoological park. Journal of Zoological Wildlife Medicine 38, 18-26.

KAPIL, S., COOPER, E., LAMM, C., MURRAY, B., REZABEK, G., JOHNSTON III, L., CAMPBELL, G., & JOHNSON, B. (2007). Canine parvovirus types 2c and 2b in North American dogs in 2006 and 2007. Journal of Clinical Microbiology 45, 4044-4047.

NETTLES, V. F., PEARSON, J. E., GUSTAFSON, G. A., & BLUE, J. L. (1980). Parvovirus infection in translocated raccoons. Journal of American Veterinary Medical Association 177, 787-789.

PARRISH, C. R., & KAWAOKA, Y. (2005). The origins of new pandemic viruses: the acquisition of new host ranges by canine parvovirus and influenza A viruses. Annual Review of Microbiology 59, 553-586.

ROMMELAERE et al, (2010) Cytokine & Growth Factor Reviews 21:185-195.

TRUYEN, U., AGBANDGE, M., & PARRISH C. L. (1994). Characterization of the feline host range and a specific epitope of feline panleukopenia virus. Virology 200, 494-503.

WIKOFF, W. R., WANG, G., PARRISH, C. R., CHENG, R. H., CHENG, M. L., STRASSHEIM, T., BAKER, S., & ROSSMAN, M. G. (1994). The structure of a neutralized virus: canine parvovirus complexed with neutralizing antibody fragment. Structure 2, 595-597.

SUGAI et al, (2009). Epitope mapping of canine distemper virus phosphoprotein by monoclonal antibodies. Microbiol Immunol. 2009 53(12):667-74.

QU et al., (2005) J. Biol. Chem. 280: 23:29568-29595.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

I claim:

1. A raccoon parvovirus (RPV) comprising the characteristics of i) Parvovirus-2 (Raccoon) of ATCC NO. PTA-11400, or ii) progeny of Parvovirus-2 (Raccoon) of ATCC NO. PTA-11400, wherein said characteristics include that said RPV comprises a nucleic acid encoding a VP-2 protein, said nucleic acid comprising nucleotide sequence SEQ ID NO: 1.

2. An immunogenic composition comprising a nucleic acid comprising the nucleotide sequence SEQ ID NO: 1, or a portion of SEQ ID NO: 1; wherein said portion of SEQ ID NO: 1 encodes an antigenic region of a VP-2 protein comprising both amino acid residue Thr at position 232 and amino acid residue Asp at position 300 of SEQ ID NO: 3, wherein said nucleic acid is present in a killed or attenuated parvovirus virion or low passage raccoon parvovirus (RPV).

3. The immunogenic composition of claim 2 wherein said killed parvovirus virion comprises the characteristics of i) Parvovirus-2 (Raccoon) having the ATCC NO. PTA-11400, or ii) progeny of Parvovirus-2 (Raccoon) of ATCC NO. PTA-11400, wherein said characteristics include that said RPV comprises a nucleic acid encoding a VP-2 protein, said nucleic acid comprising the nucleotide sequence SEQ ID NO: 1.

4. The immunogenic composition of claim 2, wherein said attenuated parvovirus virion is present in a solid carrier suitable for supralingual dissolution.

5. The-immunogenic composition of claim 2, wherein said immunogenic composition is suitable for subcutaneous administration.

6. A method of eliciting an immune response in an animal against parvovirus infection, comprising the step of administering to said animal an immunogenic composition comprising a nucleic acid comprising the nucleotide sequence SEQ ID NO: 1, or a portion of SEQ ID NO: 1, wherein said portion of SEQ ID NO: 1 encodes an antigenic region of a VP-2 protein comprising both amino acid residue Thr at position 232 and amino acid residue Asp at position 300 of SEQ ID NO: 3.

7. The method of claim 6, wherein said nucleic acid is present in a killed or attenuated parvovirus virion or low passage RPV in a killed or attenuated parvovirus virion.

8. The method of claim 7, wherein said killed parvovirus virion comprises the characteristics of i) Parvovirus-2 (Raccoon) having the ATCC NO. PTA-11400,or ii) progeny of Parvovirus-2 (Raccoon) of ATCC NO. PTA-11400, wherein said characteristics include that said RPV comprises a nucleic acid encoding a VP-2 protein, said nucleic acid comprising the nucleotide sequence SEQ ID NO: 1.

9. The method of claim 7, wherein said attenuated parvovirus virion is present in a solid carrier suitable for supralingual dissolution.

10. The method of claim 6, wherein said immunogenic composition is suitable for subcutaneous administration.

11. The method of claim 9, wherein said animal is a puppy.

12. An expression vector comprising a nucleotide sequence encoding the amino acid sequence of SEQ ID NO: 3, or a portion of SEQ ID NO: 3; wherein said portion of SEQ ID NO: 3 is an antigenic region of a VP-2 protein comprising both amino acid residue Thr at position 232 and amino acid residue Asp at position 300 of SEQ ID NO: 3, wherein said expression vector is a recombinant expression vector or a killed or attenuated viral vector.

13. The expression vector of claim 12, that is a recombinant viral expression vector.

* * * * *